United States Patent
Richardson et al.

(10) Patent No.: US 8,816,149 B2
(45) Date of Patent: Aug. 26, 2014

(54) SYSTEM FOR DETECTION AND MONITORING OF BODY EXUDATES USING A GAS EMITTING SUBSTANCE FOR USE IN INTERACTIVE TOILET TRAINING

(75) Inventors: Kathy Geralyn Richardson, Combined Locks, WI (US); John Gavin MacDonald, Decatur, GA (US); Jose K. Abraham, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 173 days.

(21) Appl. No.: 13/283,669

(22) Filed: Oct. 28, 2011

(65) Prior Publication Data

US 2013/0110064 A1   May 2, 2013

(51) Int. Cl.
*A61F 13/15* (2006.01)
*A61F 13/42* (2006.01)
*A61L 15/56* (2006.01)
*A61F 13/20* (2006.01)
*A61F 5/48* (2006.01)

(52) U.S. Cl.
CPC ........... *A61F 13/42* (2013.01); *A61F 2013/422* (2013.01); *A61L 15/56* (2013.01)
USPC ...................... 604/361; 604/385.01; 128/885

(58) Field of Classification Search
CPC ......... A61F 13/42; A61F 13/49; A61F 13/82; A61F 13/51496; A61F 5/48; A61F 2013/425; A61F 2013/422; A61L 15/56; A61L 15/24; A61K 9/7023; G08B 21/20; G09B 19/0076; Y10S 428/913; A61B 5/0002; G01N 27/121
USPC ....................... 604/361, 385.01; 128/885, 886
See application file for complete search history.

(56) References Cited

U.S. PATENT DOCUMENTS

| | | | |
|---|---|---|---|
| 4,100,324 A | 7/1978 | Anderson et al. | |
| 4,704,116 A | 11/1987 | Enloe | |

(Continued)

FOREIGN PATENT DOCUMENTS

| | | |
|---|---|---|
| EP | 1092151 B1 | 10/2008 |
| JP | 9290001 A | 11/1997 |

(Continued)

OTHER PUBLICATIONS

Arshak et al., "A review of gas sensors employed in electronic nose applications," *Sensor Review*, vol. 24, No. 2, 2004, pp. 181-198.

(Continued)

*Primary Examiner* — Justine Yu
*Assistant Examiner* — Andrew J Mensh
(74) *Attorney, Agent, or Firm* — Dority & Manning, P.A.

(57) ABSTRACT

A system for detection and monitoring of body exudates includes an absorbent article and at least one gas emitting substance incorporated within the absorbent article that can emit a gas after a liquid insult. After an insult, a device incorporating at least one gas sensitive composition can detect the gas and signal that an insult has occurred. The gas may also be detected by a non-contact gas sensor linked to a controller and signaling device which can send visual, auditory, and/or vibratory alerts. The alerts may be perceptible in an area outside the wearer's clothing or at a remote location, such as a watch, radio, computer device and/or smart phone. The system can also determine the fullness of an absorbent article and monitor dry time. The system can be used for interactive toilet training or for caring for an infant, a disabled person, an incontinent youth, or an elderly person.

22 Claims, 9 Drawing Sheets

(56) References Cited

U.S. PATENT DOCUMENTS

| | | | |
|---|---|---|---|
| 4,887,455 A | 12/1989 | Payne et al. | |
| 4,940,464 A | 7/1990 | Van Gompel et al. | |
| 5,284,703 A | 2/1994 | Everhart et al. | |
| 5,350,624 A | 9/1994 | Georger et al. | |
| 5,486,166 A | 1/1996 | Bishop et al. | |
| 5,490,846 A | 2/1996 | Ellis et al. | |
| 5,709,222 A | 1/1998 | Davallou | |
| 5,766,389 A | 6/1998 | Brandon et al. | |
| 5,820,973 A | 10/1998 | Dodge, II et al. | |
| 5,876,393 A * | 3/1999 | Ahr et al. | 604/387 |
| 6,093,869 A | 7/2000 | Roe et al. | |
| 6,097,297 A | 8/2000 | Fard | |
| 6,217,828 B1 * | 4/2001 | Bretscher et al. | 422/82.07 |
| 6,236,951 B1 | 5/2001 | Payne et al. | |
| 6,342,037 B1 | 1/2002 | Roe et al. | |
| 6,399,853 B1 | 6/2002 | Roe et al. | |
| 6,506,958 B2 * | 1/2003 | Williams | 604/361 |
| 6,570,053 B2 | 5/2003 | Roe et al. | |
| 6,575,013 B2 | 6/2003 | Bao et al. | |
| 6,645,190 B1 | 11/2003 | Olson et al. | |
| 6,683,228 B1 | 1/2004 | Pacheco, Sr. | |
| 6,723,040 B2 | 4/2004 | Brady | |
| 6,773,926 B1 | 8/2004 | Freund et al. | |
| 6,840,069 B2 | 1/2005 | France et al. | |
| 6,885,827 B2 | 4/2005 | Shushakov et al. | |
| 6,966,840 B2 | 11/2005 | Nelson | |
| 7,171,312 B2 | 1/2007 | Steinthal et al. | |
| 7,176,344 B2 | 2/2007 | Gustafson et al. | |
| 7,221,279 B2 | 5/2007 | Nielsen | |
| 7,280,441 B2 | 10/2007 | MacDonald et al. | |
| 7,335,168 B2 | 2/2008 | Rugg | |
| 7,413,550 B2 | 8/2008 | MacDonald et al. | |
| 7,449,614 B2 | 11/2008 | Ales, III | |
| 7,477,156 B2 | 1/2009 | Long et al. | |
| 7,489,252 B2 | 2/2009 | Long et al. | |
| 7,498,478 B2 | 3/2009 | Long et al. | |
| 7,582,485 B2 | 9/2009 | Boga et al. | |
| 7,592,020 B2 | 9/2009 | Boga et al. | |
| 7,667,608 B2 | 2/2010 | Ales et al. | |
| 7,700,821 B2 | 4/2010 | Ales, III et al. | |
| 7,705,194 B2 | 4/2010 | Underhill et al. | |
| 7,737,322 B2 | 6/2010 | Ales, III et al. | |
| 7,757,478 B2 | 7/2010 | Wang et al. | |
| 7,760,101 B2 | 7/2010 | Ales, III et al. | |
| 7,763,912 B2 | 7/2010 | Kasama et al. | |
| 7,800,505 B2 | 9/2010 | Pietersen | |
| 7,834,235 B2 | 11/2010 | Long et al. | |
| 7,837,663 B2 | 11/2010 | MacDonald et al. | |
| 7,837,845 B2 | 11/2010 | Abel et al. | |
| 7,915,476 B2 | 3/2011 | Long et al. | |
| 7,973,210 B2 | 7/2011 | Long et al. | |
| 7,977,529 B2 | 7/2011 | Bergman et al. | |
| 7,978,083 B2 | 7/2011 | Melker et al. | |
| 8,093,998 B2 | 1/2012 | Grossman | |
| 8,274,393 B2 | 9/2012 | Ales et al. | |
| 8,299,317 B2 | 10/2012 | Tippey et al. | |
| 8,394,074 B2 | 3/2013 | Piette et al. | |
| 2003/0054326 A1 | 3/2003 | Aaron-Barrada | |
| 2004/0147888 A1 | 7/2004 | Huang et al. | |
| 2004/0220538 A1 | 11/2004 | Panopoulos | |
| 2005/0136384 A1 | 6/2005 | Jarvis | |
| 2005/0268962 A1 | 12/2005 | Gaudiana et al. | |
| 2006/0223052 A1 | 10/2006 | MacDonald et al. | |
| 2007/0048709 A1 | 3/2007 | Ales, III et al. | |
| 2008/0255528 A1 | 10/2008 | Springer et al. | |
| 2008/0268405 A1 * | 10/2008 | Cohen et al. | 434/81 |
| 2008/0300650 A1 | 12/2008 | Gerber et al. | |
| 2009/0089928 A1 | 4/2009 | Kasbohm | |
| 2009/0155753 A1 | 6/2009 | Ales et al. | |
| 2009/0157022 A1 | 6/2009 | MacDonald et al. | |
| 2009/0221980 A1 | 9/2009 | Mosbacher et al. | |
| 2009/0302498 A1 | 12/2009 | Nedestam | |
| 2009/0326491 A1 * | 12/2009 | Long et al. | 604/361 |
| 2010/0030173 A1 | 2/2010 | Song et al. | |
| 2010/0121292 A1 | 5/2010 | Wakrim et al. | |
| 2010/0133120 A1 | 6/2010 | Varney et al. | |
| 2010/0209898 A1 | 8/2010 | Ward | |
| 2011/0152806 A1 | 6/2011 | Zhou et al. | |
| 2012/0108465 A1 | 5/2012 | Duoss et al. | |

FOREIGN PATENT DOCUMENTS

| | | |
|---|---|---|
| JP | 2000093447 A | 4/2000 |
| JP | 2003090812 A | 3/2003 |
| JP | 2007024850 A | 2/2007 |
| KR | 2010004473 U | 4/2010 |
| WO | WO 9830179 A1 | 7/1998 |
| WO | WO 0037009 A2 | 6/2000 |
| WO | WO 0249561 A1 | 6/2002 |
| WO | WO 2007073139 A1 | 6/2007 |

OTHER PUBLICATIONS

Garner et al. "Volatile organic compounds from feces and their potential for diagnosis of gastrointestinal disease," *The FASEB Journal*, vol. 21 Jun. 2007, pp. 1675-1688.

Machine Translation of Japanese Patent No. 2003-090812, Mar. 28, 2003, 9 pages.

Machine Translation of Japanese Patent No. 3147110, Dec. 18, 2008, 14 pages.

Machine Translation and English Abstract of Korean Patent No. 20090006641 (200449196, 2 pages), Jul. 2, 2009, 6 pages.

Machine Translation and English Abstract of Korean Patent No. 20110008902, Jan. 27, 2011, 6 pages.

Related U.S. Patent Applications Form.

Abstract of Japanese Patent—JP9187431 dated Jul. 22, 2997, 2 pages.

Abstract of Japanese Patent—JP2004139545 dated May 13, 2004, 2 pages.

Abstract of Japanese Patent—JP2005245695 dated Sep. 15, 2005, 2 pages.

Abstract of Korean Patent—KR20090057001 dated Jun. 3, 2009, 1 page.

Search Report and Written Opinion for PCT/IB2012/055077 dated Mar. 28, 2013, 17 pages.

* cited by examiner

SYSTEM FOR DETECTION AND MONITORING OF BODY EXUDATES USING A GAS EMITTING SUBSTANCE FOR USE IN INTERACTIVE TOILET TRAINING

BACKGROUND

Children normally wear absorbent articles such as diapers, training pants, and the like up until the time they learn to use the toilet by themselves. Adults may wear or use absorbent articles as well for incontinence, feminine care, or other applications. Additionally, caregivers may use absorbent articles such as bed pads while their children are taking part in toilet training or while caring for a sick or elderly person. Absorbent articles conventionally include a liquid permeable body-side liner, a liquid impermeable outer cover, and an absorbent core. The absorbent core is typically located in between the outer cover and the liner for taking in and retaining waste exuded by the wearer. The absorbent core can be made of, for instance, superabsorbent particles.

As to one application of the use of an absorbent article, in order to learn to use the toilet independently, a child must first learn to recognize when a bodily waste leaves his or her body so they can learn to use the toilet instead of relying on an absorbent article to contain waste such as a liquid insult. Because an insult of body waste may often occur during an activity that distracts the child to the extent that the child does not notice the insult, this recognition can represent a substantial hurdle in the training process. Also, a child's ability to recognize when an insult occurs may be hampered by the improved performance of disposable absorbent undergarments which can, for example, quickly draw and retain urine away from the wearer's skin after an insult occurs.

Close monitoring of a child by a caregiver can enhance and improve the toilet training learning process. Therefore, it would be beneficial to provide the caregiver with immediate notification and/or verification that a liquid insult, which may include urine or runny bowel movement, has occurred so that the parent or caregiver can reinforce expectations around potty training with the child while the insult event is still recent to help the child learn to stay dry. Several attempts have been made at improving toilet training aids for toilet training pants. For example, training pants that include a temperature change member and/or a dimensional change member which provide a temperature or pressure change sensation to alert the child wearing the pants that urination has occurred have been disclosed. Additional training aids have been used to alert the caregiver and/or child that urination has occurred. Such training aids include disappearing graphics disposed on the outer cover of the pants, audible alarms, vibration sensors, and light indicators that may provide visual or other sensory indication of urination.

Existing training pants having one or more training aids that alert only the wearer, or only the caregiver, to an insult of the pants promote prolonged debates between the child and the caregiver as to whether an accident has occurred. Additionally, it may take some time before detection of an insult occurs, and this delay can result in a missed opportunity to actively toilet train the child. One of the first obstacles to overcome in having a successful toilet training experience is helping the child recognize when waste leaves his or her body and ending the deniability of the occurrence of an accident by the child. There is a need, therefore, to provide a suitable absorbent article that enhances the toilet training experience for both the child and the caregiver.

Accordingly, various types of moisture, wetness or bowel movement indicators have been suggested for use in absorbent articles in order to detect the presence urine or bowel movement within an absorbent article in order to assist in toilet training. These indicators may include alarm or signaling devices that are designed to assist parents or attendants identify a wet or soiled diaper condition early on. The signaling devices produce either a visual or an audible signal.

In some embodiments, a wetness indicator has been added to an absorbent article to detect urine insults, and in other embodiments, a sensor for odor detection has been added to detect bowel movement insults. In these embodiments, conductive materials are incorporated into the absorbent article where the insult must come into close contact with the conductive materials in order for the indicator to detect an insult. For example, the conductive materials serve as conductive leads for a signaling device and form an open circuit in the article that can be closed when a body fluid, such as urine, closes the circuit. Problems, however, have been encountered in designing an absorbent article with conductive materials where the insult comes into sufficient contact with the conductive materials to close the open circuit in order to promptly alert the wearer or caregiver that an insult has occurred. Therefore, a need exists for a method for rapidly detecting the occurrence of liquid insults within an absorbent article without the use of conductive leads to provide for a more effective interactive potty training experience.

Moreover, the indicators that have been used to show that an insult has occurred within an absorbent article have been mostly visual graphics on the absorbent article itself, which can be difficult for a parent/caregiver to see without undressing the child or wearer, and which can also be difficult for the child or wearer/user to notice. Therefore, a need exists for an improved absorbent article and method of alerting a caregiver and/or wearer/user of an absorbent article that an insult has occurred to allow for closer monitoring of insults and the ability to react to and/or reinforce behavior accordingly. Additionally, a need exists for a system that can continuously monitor dry time within an absorbent article and that provides such information to a parent, caregiver, and/or wearer, allowing the parent or caregiver to reward a child/wearer for having an insult-free absorbent article.

SUMMARY

In general, the present disclosure is directed to a system including an absorbent article, at least one gas emitting substance, and at least one device comprising a gas sensitive composition, as well as a method of transmitting information to a caregiver, user, and/or wearer of the absorbent article.

The system for detection and monitoring of body exudates can include an absorbent article, at least one gas emitting substance within the absorbent article, and at least one device in association with the absorbent article. The at least one gas emitting substance can emit at least one gas when the absorbent article is contacted with a liquid insult. The gas can be emitted when any body exudate, such as urine, bowel movement, menses, or sweat comes into contact with a gas emitting substance within an absorbent article. The at least one device in association with the absorbent article, which can comprise at least one gas sensitive composition, can change appearance when the device is contacted with the at least one gas. According to the present description, the at least one device in association with the absorbent article does not have to be located on the absorbent article itself, so long as the device is in close enough proximity to the absorbent article for the at least one gas emitted from the absorbent article upon a liquid insult to cause a change in the appearance of the device, such as a color change.

In another embodiment, the system can comprise, for example, a first gas emitting substance, wherein the first gas emitting substance emits a first gas when the absorbent article is first contacted with a liquid insult, and a second gas emitting substance, wherein the second gas emitting substance emits a second gas when the absorbent article is nearing its maximum absorbent capacity. The system can also include at least one device in association with the absorbent article, comprising at least two gas sensitive compositions. The appearance of the at least one device can then change in a first manner when the device is contacted with the first gas, can change in a second manner when the device is contacted with the second gas.

The at least one gas emitting substance in the absorbent article can comprise aldehydes, benzyl ester, phenol, iso rose, sodium bicarbonate, calcium bicarbonate, or potassium bicarbonate. The at least one gas emitted from the at least one gas emitting substance can be carbon dioxide. Additionally, the at least one gas emitting substance can comprise sodium bicarbonate and citric acid and can be in a form including powders, particles, flakes, fibers, agglomerates, granules, spheres, tablets, capsules, coatings, or lotions.

In one embodiment, the at least one device in association with the absorbent article can be in close enough proximity to the absorbent article to detect the at least one gas. The at least one gas sensitive composition can comprise a pH indicator, a humectant, a basic compound, a short-chain alcohol, and water. The pH indicator can include phenolphthalein, thymolphthalein, α-naphtholphthalein, or o-cresolphthalein. The humectant includes ethanolamines, (poly)alkyleneglycols, or glycerol. The basic compound includes sodium hydroxide, sodium carbonate, or sodium acetate. The short-chain alcohol includes methanol, ethanol, propanol, or butanol.

The system for detection and monitoring of body exudates can further comprise a non-contact gas sensor, wherein the non-contact gas sensor monitors the gas concentration level of the at least one gas.

The system can further include a controller and a signaling device. The controller can be configured to detect a change above a threshold level in the gas concentration level of the at least one gas when the absorbent article is contacted with a liquid insult. An increase in the gas concentration level of the at least one gas can indicate that a liquid insult has occurred. The controller can be further configured to continuously monitor the dry time within the absorbent article. The signaling device can then alert a wearer, a caregiver, or a combination of both of the presence of a liquid insult within the absorbent article, the amount of time the absorbent article has been continuously dry, or both.

In a further embodiment, the signaling device can generate at least one alert selected from an auditory signal, a vibratory signal, a visual signal, or a combination thereof. The alert can be transmitted to a watch, radio, smart phone, or computer device at a remote location. The computer device, smart phone, or a combination of both can be adapted to receive data from the signaling device, generate at least one report utilizing at least a portion of the data, and provide a user access to the data and the at least one report. The signaling device can also be deactivated at or near the absorbent article or remotely. The system can also include a housing unit containing the non-contact gas sensor, controller, and signaling device such that the housing unit is in close enough proximity to the absorbent article to detect the at least one gas.

In yet another embodiment, the present disclosure describes a signaling device comprising at least one gas sensitive composition, a non-contact gas sensor, and a controller. The at least one gas sensitive composition allows the signaling device to change in appearance when the signaling device is contacted with at least one gas emitted by at least one gas emitting substance within an absorbent article when the absorbent article is contacted with a liquid insult. The non-contact gas sensor can monitor gas concentration levels of the at least one gas. The controller can be configured to detect changes above a threshold level in the gas concentration levels of the at least one gas when the absorbent article is contacted with a liquid insult. Additionally, the controller can be configured to continuously monitor the dry time within the absorbent article. The signaling device can alert a user of the absorbent article, a caregiver, or a combination of both of the presence of a liquid insult within the absorbent article, the fullness of the absorbent article, and the amount of time the absorbent article has been continuously dry.

The present disclosure also describes a method of transmitting information to a user of an absorbent article, a caregiver, or a combination of both. The method can comprise monitoring the presence of at least one gas emitted from at least one gas emitting substance within the absorbent article. The at least one gas emitting substance can emit at least one gas when the absorbent article is contacted with a liquid insult. The method can also comprise alerting the user, caregiver, or a combination of both of the liquid insult.

In another embodiment, the method can comprise monitoring the presence of a first gas, wherein a first gas emitting substance can emit the first gas when the absorbent article is first contacted with a liquid insult and monitoring the presence of a second gas, wherein a second gas emitting substance can emit the second gas when the absorbent article is nearing its maximum absorbent capacity. The method can also comprise providing information to the user, caregiver, or both. The information can be provided by at least one device in association with the absorbent article, wherein the at least one device in association with the absorbent article comprises at least two gas sensitive compositions. The appearance of the at least one device can change in a first manner when the device is contacted with the first gas can change in a second manner when the device is contacted with the second gas.

In a further embodiment of a method of transmitting information, a non-contact gas sensor can detect the presence of the at least one gas when the absorbent article is contacted with a liquid insult. A controller can be configured to detect a change above a threshold level in the gas concentration level of the at least one gas and can be configured to continuously monitor the dry time within the absorbent article. A signaling device can also alert a wearer, user, or both of the presence of a liquid insult within the absorbent article, the amount of time the absorbent article has been continuously dry, or both. The signaling device can generate at least one alert selected from an auditory signal, a vibratory signal, a visual signal, or a combination thereof, and the alert can be transmitted to a watch, radio, smart phone, computer device, or a combination thereof at a remote location. The at least one alert can be perceptible outside the absorbent article and even outside the wearer's clothing and can be deactivated at or near the absorbent article or remotely.

In one embodiment, the computer device or smart phone can be adapted to receive data from the signaling device, generate at least one report utilizing at least a portion of the data, and provide the user access to the data and the at least one report. The user, caregiver, or a combination of both can be provided with information from the at least one report to indicate the number of insults contained within an absorbent article. The user, caregiver, or a combination of both can also be provided with information from the at least one report to indicate the fullness of the absorbent article and can also be provided with information from the at least one report to indicate the amount of time the absorbent article has been continuously dry, in order to monitor and facilitate interactive toilet training.

Other features and aspects of the present disclosure are discussed in greater detail below.

BRIEF DESCRIPTION OF THE DRAWINGS

A full and enabling disclosure, including the best mode thereof to one of ordinary skill in the art, is set forth more particularly in the specification, including reference to the accompanying figures in which.

DETAILED DESCRIPTION

Figure 1:
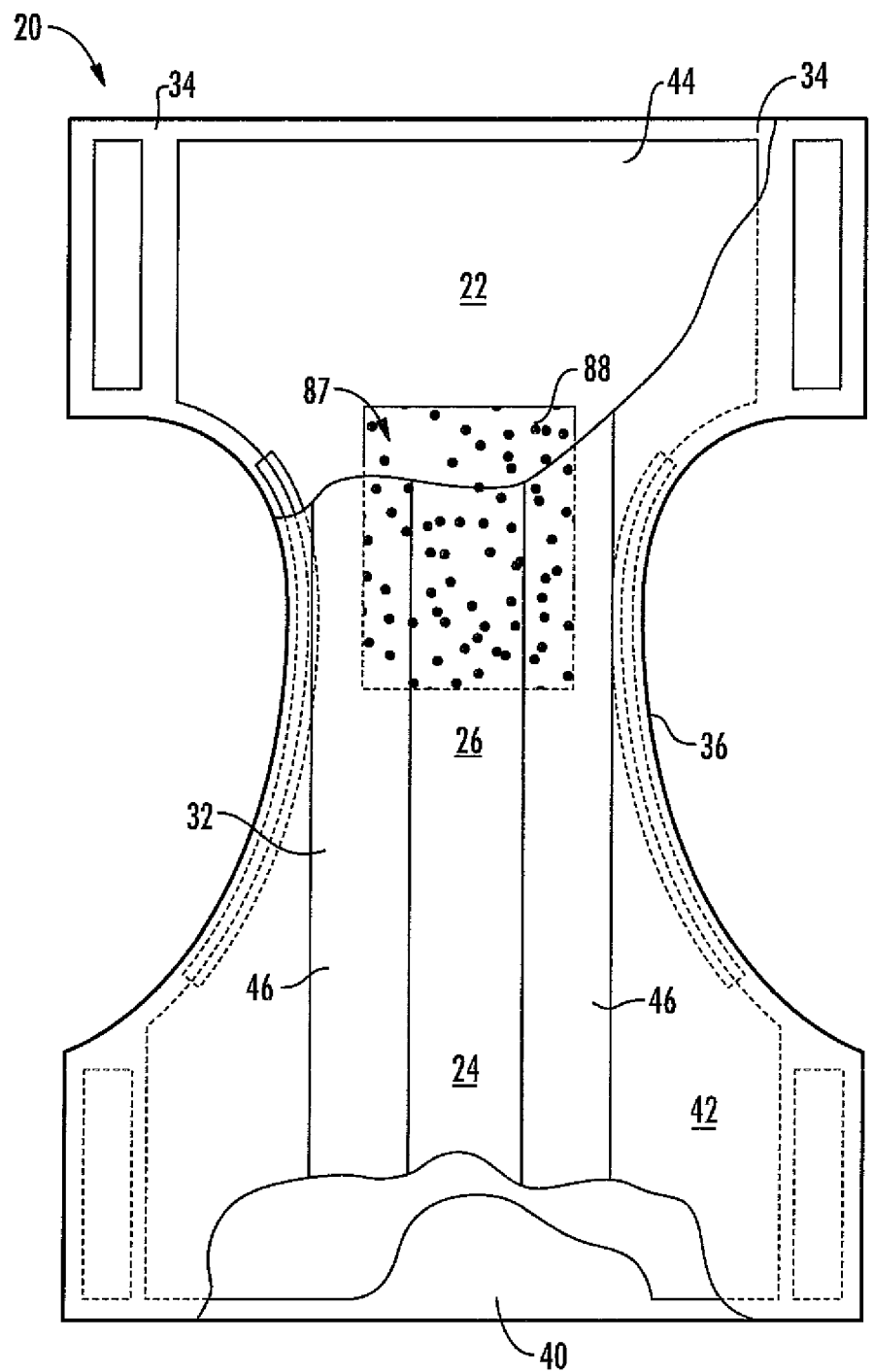
FIG. 1 is a plan view of an absorbent article containing a gas emitting substance within the absorbent core at the region of insult that emits a gas when the absorbent article is contacted with a liquid insult.

Reference will now be made in detail to various and alternative exemplary embodiments and to the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment can be used on another embodiment to yield a still further embodiment. Thus, it is intended that the present disclosure includes modifications and variations as come within the scope of the appended claims and their equivalents.

In general, the present disclosure is directed to a system and method for providing information about an absorbent article to a caregiver, user, and/or wearer. The information can be linked to the occurrence of insults within an absorbent article such as a diaper or training pant worn by a child or used by another person, such as a bed pad or mat. While many of the figures may show an embodiment of a training pant for a child, it is to be understood that other absorbent articles can be used, such as bed pads, adult incontinence products, or youth incontinence products. The absorbent article may also be, for instance, a feminine hygiene product, a medical garment, a bandage, and the like. While the present disclosure discusses using the system and method for interactive toilet training as one application, the embodiments may have applications outside the toilet training context, such as in monitoring for excessive clothing, fever, or moisture in any environment. The present disclosure may also have multiple applications within the toilet training context itself, and in one embodiment may be used on the seat of a toilet or on the floor around the toilet to detect when a child may miss the toilet when voiding his or her bladder as he or she learns to use the toilet.

The absorbent article for interactive toilet training may include a gas emitting composition that works with a device that may incorporate gas sensitive ink in order to alert a caregiver or wearer/user of a liquid insult. In another embodiment, it may include an electronic gas sensor that may be configured to indicate the presence of a liquid insult through the use of auditory, vibratory, and/or visual signals in addition to ink. It may also send alerts wirelessly to a radio, computer device, or smart phone. It is also possible that the device that incorporates gas sensitive ink and the electronic sensor can be used together to alert the user/wearer and/or a caregiver who may not be nearby to notice a change in the device that incorporates gas sensitive ink. The electronic sensor may be housed with a controller and a signaling device within a housing unit that attaches, for example, at or near the waist opening of a training pant or an incontinence product or on the edge of a bed pad. However, depending on the sensitivity of the types of sensors that may be used, attachment to the absorbent article itself may not be necessary to detect a liquid insult. For example, the wearer or user of the absorbent article may be able to wear a badge, watch, sticker, tattoo, or other device that can house the gas sensitive ink. The electronic gas sensor and the device that incorporates a gas sensitive composition instead of an electronic sensor may not have to be in close proximity to the article so long as they are close enough to detect the gases emitted from the one or more gas emitting substances within the absorbent article. For example, the electronic gas sensor and/or device with the gas sensitive composition may be located within a 12 inch radius of the absorbent article, or they may be located even farther away from the absorbent article. It should be noted that the device incorporating gas sensitive ink may be used in combination with the electronic sensor to provide various types of alerts as discussed above. Generally, the absorbent article itself may be disposable, meaning that it is designed to be discarded after a limited use rather than being laundered or otherwise restored for reuse. Additionally, the device that incorporates gas sensitive ink may be disposable or reusable, and the electronic gas sensor is designed to be reusable.

In one embodiment, an absorbent article may contain a gas emitting substance that emits a gas when a liquid insult such as urine or runny bowel movement occurs, and the device incorporating a gas sensitive composition/ink or the electronic gas sensor can monitor the gas emitted from the gas emitting substance. One advantage of the addition of a gas emitting substance is that the volume of gas produced immediately after an insult may be so high that an insult can be detected more quickly than when gases only associated with a liquid insult are present. Gases associated with a urine or bowel movement insult may not be present in quantities as large as associated with the gas emitting substance, which may cause detection of the insult to take a longer amount of time. On the other hand, the gas associated with a gas emitting substance can be formed when liquid contacts the absorbent article, even in very small quantities. Large quantities of gas can be produced and may rapidly diffuse and reach a device containing at least one gas sensitive composition or an electronic gas sensor that is nearby.

For example, sodium bicarbonate/citric acid mix or another substance that can emit a gas may be placed within the absorbent article during the manufacturing process or at some other time before the absorbent article is used by the consumer. The substances that may be included in the absorbent article can be in the form of powders, particles, flakes, fibers, agglomerates, granules, spheres, tablets, capsules, coatings or lotions and may or may not be encapsulated. For example, for one reaction, a powder or particles of the gas emitting substance may be placed within a composite material of the absorbent article or in a separate material that can be introduced to the absorbent article, such as a panty liner. As a liquid insult comes into contact with the powder or particles, a reaction producing a gas can result.

For a more delayed reaction, which can be used to detect the amount of fullness within an absorbent article, a microencapsulated film or shell containing the gas emitting substance can be placed inside the absorbent article. Alternately, one gas emitting substance may be placed in the direct insult region, such as the crotch region, while another gas emitting substance may be placed on the exterior of the absorbent article or around the edges of the absorbent material within the absorbent article. Gas emitting substances can also be placed in concentric rings, each of which can produce a gas to initiate a distinct reaction such as a color change. Then, distinct gas sensitive compositions can be placed in one or more devices to indicate the level of fullness within the absorbent article. In this way, the user and/or caregiver can distinguish between an insult being present and the absorbent article being near full capacity. Additionally, various gas sensors linked to different auditory, vibratory, and/or visual alerts can be used to determine if an insult had occurred or if the absorbent article is nearing full capacity.

In some aspects, the gas emitting substance can be encapsulated in an aqueous-soluble shell material. For example, if the gas emitting substance includes an acid and a base, the acid and the base may be separately encapsulated in a soluble encapsulation material to keep the components separated until wetted. Alternatively, the acid and base components may be encapsulated together if reactivity between the acid and the base in the absence of an aqueous liquid is not a concern. An optional surfactant can also be separately encapsulated, or may be encapsulated with the acid and/or the base in this example. The shell material used for encapsulation may be suitably constructed of a material such that it will release the gas emitting substance upon contact with aqueous liquids such as urine, complex fluids or other body exudates. The aqueous liquids can cause the shell material to solubilize, disperse, swell, or disintegrate, or the shell material may be permeable such that it disintegrates or discharges the encapsulated material upon contact with the aqueous liquids.

Suitable shell materials include cellulose-based polymeric materials (e.g., ethyl cellulose), carbohydrate-based materials (e.g., starches and sugars) and materials derived therefrom (e.g., dextrins and cyclodextrins) as well as other materials compatible with human tissues. Water soluble films such as polyvinyl alcohol and polysaccharide film, available from MonoSol, LLC in Merrillville, Ind., can be used to encapsulate the gas emitting substance. The shell or film thickness may vary depending upon the substance that is encapsulated, and is generally manufactured to allow the encapsulated substance to be covered by a thin layer of encapsulation material, which may be a monolayer or thicker laminate, or may be a composite layer. The layer should be thick enough to resist cracking or breaking of the shell during handling or shipping of the product or during wear or use which would result in breakage of the encapsulating material. The shell material should also be constructed such that humidity from atmospheric conditions during storage, shipment, or wear will not cause a breakdown of the microencapsulation layer. In some aspects, at least one of the stimulation layers can further comprise a beneficial additive which provides an additional benefit to the user. Exemplary beneficial additives include surfactants, ion exchange resin particles, moisturizers, emollients, perfumes, fluid modifiers, odor control additives, pH buffering for the skin, vaginal health-care additives, coating materials for skin health, vitamins, medicines, and the like.

The gas emitting composition may also be placed on the surface of the absorbent article to facilitate a faster notification of an insult because the fewer layers of absorbent article the gas has to diffuse through, the faster the gas can reach the gas sensitive ink or sensor to alert a child and/or caregiver of an insult. As noted, while the gas emitting substance can be incorporated into the absorbent article itself, such as by being sprinkled or introduced in some other fashion into the absorbent core, it may also be incorporated into a material such as a panty liner that may be added to the absorbent article at a later time regardless of the form of the gas emitting substance (powder, particles, flakes, fibers, agglomerates, granules, spheres, tablets, capsules, coatings, lotions, etc.). Upon the occurrence of a liquid insult, the gas emitting substance, which can be a sodium bicarbonate/citric acid powder mix, for example, can emit a gas that is not present in a urine or bowel movement insult. This gas can be carbon dioxide or another gas, and when the gas is generated and diffused, it can then be detected by a reaction with a gas sensitive composition or a non-contact gas sensor for the particular gas, such as carbon dioxide. The gas can be produced after an acid-base reaction. This requires an acid and a base, although it can also include amphoteric substances that can react as either an acid or a base.

For instance, sodium bicarbonate is an amphoteric compound that causes aqueous solutions to be mildly alkaline. The reaction of sodium bicarbonate and citric acid results in a salt and carbonic acid, which readily decomposes to carbon dioxide and water. For example, when 1 gram of sodium bicarbonate/citric acid mix was placed in an absorbent article and 10 milliliters of deionized water was introduced, the resulting carbon dioxide produced had a volume of 130 milliliters. The reaction will be the same and will produce the same amount of carbon dioxide with urine instead of deionized water as well. The large volume of carbon dioxide produced may have the advantage that the device with gas sensitive ink or the electronic gas sensor may be placed on the outer clothing of the wearer of the absorbent article due to the amount of gas generation and its ability to diffuse over greater distances, which means that it can be easier for the wearer or caregiver to notice that a liquid insult has occurred. In other words, a small volume of liquid insult can lead to large gas generation which can then lead to almost immediate sensing of an insult, even if the device with gas sensitive ink or the electronic gas sensor is not attached to the absorbent article containing the gas emitting substance. Note that although the gas produced by the reaction of the sodium bicarbonate and citric acid with a liquid insult can be carbon dioxide, the present disclosure is not limited to the use of just sodium bicarbonate and citric acid to produce carbon dioxide. Other substances can be used, such as aldehydes, benzyl ester, phenol, iso rose, other fragrance ingredients, and etc., which can be encapsulated into a water soluble membrane such as polyvinyl alcohol and polysaccharide film. Additionally, bicarbonates such as sodium, calcium, potassium, etc. can be used for generating a gas, such as carbon dioxide, that can be detected by a gas sensitive composition, although the gas emitted does not have to be carbon dioxide.

One process by which the gas emitting substance can be incorporated into an absorbent article is described in U.S. Patent Application 2011/0152806A1 published Jun. 23, 2011 by Zhou, et al., which is incorporated herein by reference, although other processes known to those skilled in the art may be used. Also, see the text below in the discussion of FIG. 1 for a description of how the gas emitting substance may be incorporated into an absorbent article.

When a liquid comes into contact with the gas emitting substance, which may be but is not limited to a sodium bicarbonate/citric acid mix, the gas produced can then be detected, for example, by a gas sensitive composition or ink. Any non-toxic substance may be used so long as the gas produced upon a liquid insult is distinct from a gas produced by the liquid insult itself. In this manner, the detection device such as a device that incorporates a gas sensitive ink or other device does not act as a chemical nose as to a particular type of insult and instead detects a separate gas that is produced as a result of a reaction between an insult and a separate substance within the absorbent article.

The device incorporating a gas sensitive ink may be a badge, watch, sticker, or other device that a child may wear on the outside of his or her clothing. Generally, an image such as a star, flower, rainbow, or other image that is pleasing to a child may be present on the device as long as there is no liquid insult within the absorbent article. However, once a liquid insult occurs, the image may fade, disappear, or change into an image that may not be pleasing to a child, such as, but not limited to, a black or brown circle, as the ink used in the image reacts with the gas from the gas emitting substance. On the other hand, an image may appear where there was no image previously to indicate that an insult has occurred. For example, a colored badge or sticker could be worn showing a star or smiley face, and then as an insult occurs, the star could disappear or the smiley face could change to a frown instead. The frown can appear as a gas emitted after an insult contacts a gas sensitive ink or composition. Additionally, the images on the device containing at least one gas sensitive composition can change as different levels of fullness are reached within the absorbent article, and different gases could be used to cause different color changes in order to distinguish between an insult and a level of fullness. Combinations of appearing and disappearing inks can thus be used alone or in combination to alert a caregiver/user or wearer of an insult or the levels of fullness within an absorbent article. The different appearances of the device based on the presence or absence of an insult or the amount of fullness may be used in toilet training as positive or negative reinforcement. Additionally, the device may be worn on the outside of the child/wearer's clothing because the gas generated is sufficient to reach an area outside the absorbent article, such as an object that is 12 inches, or possibly farther, away. For example, the child may wear a badge on a shirt or pants or a watch on his or her wrist, or the badge or other device may be placed near the child on a bed pad. This may allow the parent or caregiver/user, as well as the child, to monitor for liquid insults as well as fullness within an absorbent article.

In one embodiment, the compositions or inks used in the device may be sensitive to carbon dioxide when a sodium bicarbonate/citric acid mixture is used as the gas emitting substance, although other compositions that react with other gases emitted from various gas emitting substances may also be used alone or combination with each other. The main components of inks that may react with carbon dioxide are alkali salts, water, lower alcohols, and pH indicators with color change transitions ranging from 8 to 10. When the ink on the surface is exposed to carbon dioxide at levels greater than atmospheric, the alkali salts may react with the carbon dioxide, which leads to the production of acids. The generation of acids can result in a change in pH and thus a color change for the device such as a badge, watch, or sticker. This ink technology is inexpensive and commercially available, and there may be a diverse selection of compounds that are available for use in the ink. Additionally, the color may be quite tunable if the appropriate pH indicator is incorporated into the ink.

For example, a carbon dioxide based ink where the color disappears or fades as the ink reacts with carbon dioxide may include the following components: suitable pH indicators, dry preventing agents or humectants, appropriate basic compounds, short-chain (low) alcohols, and water. Suitable pH indicators may include phenolphthalein, thymolphthalein, α-naphtholphthalein, o-cresolphthalein, and the like. Potential humectants may include ethanolamines, (poly)alkyleneglycols, glycerol, and the like. Appropriate basic compounds may include sodium hydroxide, sodium carbonate, and sodium acetate, among others. Additionally, suitable short-chain alcohols may include methanol, ethanol, propanol, butanol, etc.

For ink that may disappear or fade when there is a reaction with carbon dioxide, a pH indicator may be needed that exhibits a clear color change between a basic to neutral pH transition. For example, phthalein-based indicators may be used as they produce noticeable color transitions when when a pH decrease from about to 10 about 7. For example, α-naphtholphthalein has a pH range of about 7.3 to 8.7 and a color transition from reddish brown to blue/green. O-cresolphthalein has a pH range of about 8.2 to 9.8 and a color transition from colorless to purple. Phenolphthalein has a pH range of about 8.3 to 10 and has a color transition from colorless to violet. Thymolphthalein has a pH range of about 9.3 to 10.5 and has a color transition from colorless to blue. Additionally, other indicators may be used for disappearing inks so long as they provide a noticeable color change during a transition from a basic to neutral pH. The ink compositions may be prepared using ethanolamine, triethanolamine, N-methyl ethanolamine, N-(β-aminoethyl)ethanolamine, diethylethanolamine, glycerol, ethyleneglycol, and poly(ethyleneglycol) and mixtures thereof as the respective dry preventing agents.

An advantage of the present disclosure is that the gas emitted from a gas emitting substance that may be located in or on the absorbent article is emitted in very high concentrations and reacts with a gas sensitive composition so that there is less chance for false readings due to low levels of moisture or flatulence that would not necessarily indicate the presence of a liquid insult within an absorbent article. Additionally, in order for the gas being detected to even be generated, a liquid insult must occur, thus reducing the risk for false positives that may exist with other devices. The United States Patent Application entitled "Absorbent Articles with Multiple Active Graphics" to Ruman, et al. and assigned application Ser. No. 12/976,734 describes various inks that may also be used with absorbent articles and is incorporated herein by reference. The compositions described in Ruman, et al. may be initially colorless and manifest color from an originally colorless state or they may initially manifest color that may disappear upon the occurrence of a liquid insult. These compositions or inks may be used alone or in combination with the disappearing compositions described above in designing the images or graphics that may appear on an absorbent article itself as well as on a device such as a badge, watch, or sticker upon the occurrence of a liquid insult. The dye technology that may be used is further described in United States Patent Application Publication Number 2010/0030173 to Song, et al. entitled "Absorbent Products with Wetness Sensors," which is incorporated herein by reference.

In addition to using a device incorporating gas sensitive ink or composition to signal that a liquid insult has occurred, the present disclosure may also use a non-contact gas sensor alone or in combination with the device incorporating the gas sensitive ink or composition. The gas sensor may be able to detect gases that may be emitted by at least one gas emitting substance when an insult comes into contact with the gas emitting substance. For example, one gas that may be emitted is carbon dioxide. The gas sensor may also be configured to detect gases associated with an insult itself.

A child, wearer or caregiver/user can monitor the conditions within an absorbent article through the use of a non-contact gas sensor, a controller, a signaling device, a transmitter and a receiver. The controller can be a microprocessor such as a multicomponent data analyzer. The non-contact gas sensor, controller and signaling device may be contained within a single housing unit. In another embodiment, the non-contact gas sensor, controller, and transmitter may be separated from each other (i.e., not contained in a single housing unit). The non-contact gas sensor can monitor a gas that is emitted by a gas emitting substance after a liquid insult within an absorbent article. The gas that is monitored is distinct from gases emitted by volatile compounds (VCs) as short-chain fatty acids (acetic acid), ammonia, methane, hydrogen sulfide, dimethyl sulfide, thiols such as mercaptans, skatole and indole that are present in a liquid insult such as urine or runny bowel movement. As used herein, the term "volatile compound" is meant to include both the organic and inorganic metabolic gases and compounds produced by microbes present in body wastes or exudates.

Particular VCs may be associated with one or more types of body exudates, including but not limited to urine and bowel movement. VCs commonly associated with urine include, for example, ammonia compounds (e.g., ammonia hydroxide), short-chain ($C_1$-$C_2$) acids (e.g., acetic acid), medium length ($C_8$-$C_{10}$) aldehydes (e.g., nonanal), ketones (e.g., methyl ethyl ketone), cresol (e.g., methylphenol), dimethyl disulfide, trimethylamine, limonene (e.g., 4-isopropyl-1-methylcyclohexane), acetic acid, methyl benzoate, benzamide, benzaldehyde, and triethylamine, among others. VCs commonly associated with bowel movement or feces include, for example, skatole (e.g., 3-methyl-1H-indole, 3-methylindole, etc.), thiols such as mercaptans (e.g., 2-mercaptoethanol), hydrogen sulfide, short-chain fatty acids (e.g., myristic acid), methanethiol (e.g., 2-mercaptoethanol), and dimethylsulfide, among others. Some of the most common VCs in bowel movement include short-chain fatty acids, indole and thiols such as mercaptans. Other VCs in bowel movement include but are not limited to 4-methylphenol, pentanoic acid, 2- or 3-methylfuran, carbon disulfide, butanoic acid, ethanoic acid, 6-methyl-5-hepten-2-one, 2-pentanone 2-butanone, 2,3-butanedione, acetaldehyde, acetone, 2-heptanone, propanal, hexanal, and 3-methyl. The present disclosure can monitor gases emitted from a gas emitting substance that are distinct from the gases emitted by the aforementioned volatile compounds upon the occurrence of a liquid insult, although it may also monitor gases associated with the aforementioned VCs. The gas that can be monitored is present in much higher amounts than the gases associated with VCs in body exudates, and this therefore may allow the non-contact gas sensor to be positioned a greater distance away from the absorbent article in an expanded sensing area, such as up to 12 inches or more away, although it can be positioned about the waist opening of an absorbent article such as a training pant or on the edge of an absorbent article such as a bed mat.

A non-contact gas sensor and controller combination can monitor a gas that is emitted from a gas emitting substance upon a liquid insult within an absorbent article. The non-contact sensor can detect a particular gas such as carbon dioxide, and then a controller such as a microprocessor may use pattern recognition or some other means to identify the particular gas. As the gas generated by the reaction of the gas emitting substance in the absorbent article with a liquid insult comes into contact with the non-contact gas sensor, the sensor is designed to have the ability to identify a gas associated with a particular substance. The non-contact gas sensor is commercially available and can be a conductivity sensor, a piezoelectric sensor, an optical sensor or a metal oxide semiconductor (MOS) sensor. MOS sensors are often used because of their high sensitivity to a wide range of organic compounds and gases. However, other types of sensors are also commercially available, including but not limited to those mentioned above as well as sensors incorporating NDIR (Non-Dispersive Infrared) technology, organic thin film transistors, chemiresistors, etc.

One way in that a sensor works is that when a sample of a particular gas comes into contact with a sensor designed to monitor that gas, the sensor undergoes a physical or chemical change. This, in turn, causes a change in an electrical signal, which may be detected by a controller. The controller can be pre-conditioned to recognize that certain patterns are associated with certain gases, and it is thus able to detect a gas emitted from a particular gas emitting substance incorporated into an absorbent article after a reaction between a liquid insult and the gas emitting substance occurs.

Determining what sensor to use in the non-contact gas sensor depends on the gas to be detected. Individual sensors designed to measure gas concentration levels associated with a particular gas can be selected. The suitability of a particular sensor material for monitoring a gas emitted by the gas emitting substance can be easily and readily determined by one skilled in the art based in part on the disclosure herein.

In one embodiment, a controller coupled to the non-contact gas sensor can make a decision about the presence of the gas after analyzing signals or data from the non-contact gas sensor. The non-contact gas sensor and controller may first measure for ambient conditions where any deviations from the pre-determined value of the gas to be measured are recorded in a controller. For example, the level of carbon dioxide present in the atmosphere can be pre-determined and recorded as the threshold level of carbon dioxide if that is the gas to be measured. Then, the controller may only send a signal to a signaling device that an insult has occurred if the level of carbon dioxide it measures exceeds the pre-determined threshold level of atmospheric carbon dioxide.

The controller may be "trained" to detect a particular level of a gas and associate that gas concentration level with the presence of a liquid insult such as urine or runny bowel movement within an absorbent article. From the raw signal data measured by the non-contact gas sensor, the controller can analyze the signal data coming from the sensor, which then serves as a basis the determination that a liquid insult has occurred and is identified. For example, retaining signal values over time, one may determine the peak or quantile of the signal or pre-processed signal (e.g., moving average, gradient, or other combination of pre-processing steps) to attain an estimate for the magnitude of the signal. On the same or different pre-processed signals, one can also determine a point estimate of the signal slope, including, but not limited to, the maximum, minimum, mean, quantile or other measure. An additional measure can include the integrated area of the pre-processed signal. Still other quantities are also possible, and it should be noted that signal magnitude, slope, and area only serve as examples of point estimate features.

In another embodiment, various classifiers can be developed from the primary or secondary features in order to determine the number of insults over time or the amount of time between the insults. Additionally, other potential indicators of child or wearer/user health may also be developed from the primary or secondary features. Training data may be used to develop the pattern classifier within the controller in order to distinguish between ambient conditions and when a liquid insult has occurred. Model variables corresponding to features may be added to maximize the between class variance and minimize the predicted residual sum of squares for the test, or unseen, data. The classifiers include, but are not limited to, linear/non-linear discriminant analysis techniques, neural networks, classification and regression trees, and other techniques that create a continuous or discrete signal to the user.

In another embodiment, the controller may continuously monitor the dry time within an absorbent article. From information provided by the non-contact gas sensor and controller that may be sent to a signaling device, the caregiver may be able to monitor from close by or from a remote location the length of time that the wearer has worn an absorbent article without the occurrence of a liquid insult of urine or runny bowel movement. Based on inputs from the caregiver, the signaling device can transmit an alert to the child after the absorbent article has been dry for set periods of time. The alert can be in the form of a song and/or display that is pleasing to the child. This alert can be transmitted from the signaling device itself. In another embodiment, the caregiver and/or user could receive an alert as to how long the absorbent article has been continuously dry.

The information transmitted to a computer device or smart phone regarding the amount of continuous dry time can be communicated to the caregiver in different ways. The amount of continuous dry time can be averaged over hours, days, weeks or months. In one embodiment, the dry time can be segmented according to typical child behavior. For example, an average dry time can be calculated for different times of the day, such as the morning, afternoon and evening. A separate dry time can also be calculated while the child is sleeping.

In one embodiment, the dry time can be recorded and stored by communicating with an electronic communication medium, such as an interactive website that may be accessible via the Internet using a smart phone or computing device. This allows for dry times to be monitored over a length of time to determine whether progress is being made after a caregiver has started toilet training a child.

The controller can read gas levels monitored by the non-contact gas sensor and can then analyze the data to identify a liquid insult based on the presence of a gas emitted by a gas emitting substance upon the occurrence of a liquid insult within the absorbent article. The controller can first read initial gas concentration levels monitored or detected by the non-contact gas sensor. These levels can then be calibrated to reflect a null value or zero, and then any change from these calibrated values may be monitored. If a change in gas concentration level above a certain threshold occurs, the controller may trigger an alarm through a signaling device.

The signaling device, alone or in addition to the device incorporating a gas sensitive ink discussed above, can provide power to the controller while also including an audible, visual and/or vibratory signal or alert that indicates to the user and/or caregiver the presence of a liquid insult. Any alerts from the signaling device can also be remotely activated or displayed on smart phones or computers. In another embodiment, an alert may also be sent to a wireless radio. In yet another embodiment, the alert may be sent to an indicator or display on the housing unit or some other area near the absorbent article so that the wearer or another person who may be close by, such as a caregiver, can be alerted of an insult. Once an alert is received by a wearer or caregiver that an insult has occurred, the interactive toilet training process can be initiated. Additionally, alerts as to the absorbent article being dry for a continuous amount of time can also initiate the interactive toilet training process through positive reinforcement or by allowing the parent/caregiver to determine next steps based on the amount of dry time. The alerts can be deactivated remotely or at or near the signaling device itself. The alerts may also be turned off if the child/wearer needs to take a break from the toilet training process or removed from around or near the absorbent article completely. As alerts may be visual, auditory, and/or vibratory and/or sent remotely to a radio, computer device or smart phone, a caregiver can modify the type of alarm based on the level of discreteness that is desired. For example, if the caregiver is at home with the wearer of the article, it may be more appropriate to have an auditory alert, while if the caregiver and wearer are in a public place, a remote alert sent to a smart phone or a silent alert such as a visual alert may be more appropriate.

Although the absorbent article itself is disposable, the non-contact gas sensor, controller, and signaling device or other devices used to alert a child/user or parent/caregiver may be reusable from article to article. In this regard, the present disclosure is particularly directed to the use of a non-contact gas sensor, controller, signaling device and attachment mechanisms that allow for quick and accurate detection of liquid insults to allow for interactive toilet training opportunities at a time close to when an insult has occurred. Whether a device with gas sensitive ink is used, or a non-contact gas sensor, controller and signaling device is used, the detection of a liquid insult can be almost immediate, due to the fast diffusion of gas in the air space, which is based on the large amount of gas produced by a gas emitting substance when contacted with only a small amount of liquid.

If a non-contact gas sensor, controller, and signaling device are used, they may be contained in a housing unit. The housing unit may be connected at or near the waist opening of the absorbent article via a clip on device or other means, or the housing unit may be located nearby, such as up to about 12 inches or more away. If the non-contact gas sensor is part of an embodiment that includes a housing unit, small holes can be located on the housing unit in a manner that results in the holes being exposed to an area near the absorbent article to allow for sufficient gas sampling by the non-contact gas sensor. Alternatively, the housing unit may be connected to the absorbent article via other means, so long as the non-contact gas sensor is sufficiently close to the absorbent article to detect the gas generated by the gas emitting substance. The non-contact gas sensor, the controller and the signaling device can all be contained within a single housing unit that attaches to the waist opening of a diaper or training pant or to the edge of an absorbent article such as a bed pad or mat via use of a clip-on or other device. The housing unit may also be placed outside the perimeter of the absorbent article, such as on the clothing of the wearer.

As described above, the non-contact gas sensor in combination with the signaling device may be configured to indicate the presence and number of liquid insults within an absorbent article which indications can then be used as part of toilet training. However, the particular targeted liquid waste may vary depending upon the particular type of absorbent article and the desired application. For instance, in one embodiment, the absorbent article comprises a diaper, a training pant, or the like and the signaling device is configured to indicate the presence of urine. Additionally, the signaling device may be configured to indicate the presence of any other body fluids of the wearer of the absorbent article.

Figure 2:
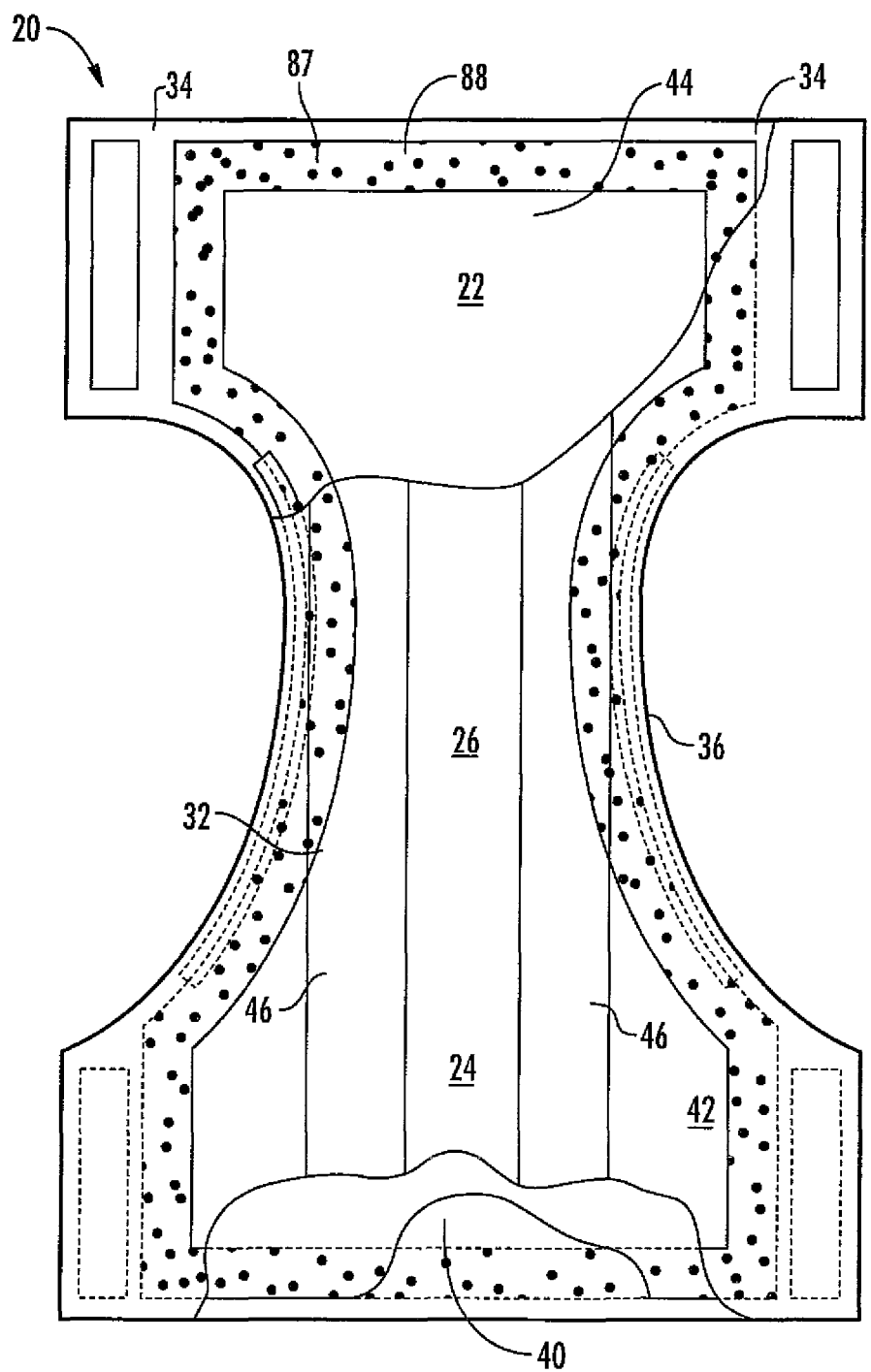
FIG. 2 is a plan view of an absorbent article containing a gas emitting substance around the perimeter of the absorbent article within the absorbent core that emits a gas when the absorbent article to indicate fullness related to one or more liquid insults within the absorbent article.

Referring to FIGS. 1 and 2, the disposable absorbent article 20 of the present invention also includes a gas emitting substance composite 88 that is positioned and adapted within the absorbent article 20 to come into contact with a liquid insult within the absorbent article. The gas emitting substance composite can be selectively placed wherever a body exudate is expected to be present, such as in the crotch region of the absorbent article. Note that while FIG. 1 shows that the gas emitting substance composite is manufactured as part of the absorbent article, it may be attached to the absorbent article such as in the form of a panty liner. Additionally, the gas emitting substance may be in the form of a coating or lotion on the surface of the absorbent article closest to the wearer in order to provide the fastest reaction time upon the occurrence of an insult. The gas emitting substance composite 88 can have a longitudinal-direction and a transverse-direction, which together can form a plane when in a laid-flat condition, hereinafter referred to as the "x-y plane." The gas emitting substance composite 88 may be placed in the absorbent article such that it can define a body-facing surface 87 intended to be disposed toward the wearer in use (i.e., an inner surface) and a garment-facing surface (not shown) intended to be disposed away from the wearer in use, opposite the member inner surface (i.e., an outer surface).

The gas emitting substance composite 88 can be placed within the absorbent article in any desired shape, and if an absorbent article such as a diaper or training pant is used, it can be placed in the region of direct insult, such as the crotch, in order to detect an insult as shown in FIG. 1. For example, it may have a 2-dimensional or 3-dimensional configuration, and may be rectangular shaped, triangular shaped, circular-shaped, oval shaped, race-track shaped, 1-shaped, generally hourglass shaped, T-shaped and the like. In some aspects, the gas emitting substance composite 88 can have no particular defined shape, but rather can have a random shape. Thus, the dimensions in at least the x-y plane can vary as desired. The gas emitting substance composite 88 can also has a thickness dimension in the z-direction as desired. Additionally, as shown in FIG. 2, a gas emitting substance composite 88 that may contain a different gas emitting substance to react with a different gas sensitive composition to produce a different color change may be placed certain distances away from the center of the absorbent article, such as around the perimeter of the absorbent core 44. This can be used to indicate the fullness of an absorbent article. Alternately, the composite could be placed in concentric rings (not shown) instead of around the perimeter. In addition to determining fullness, the placement of the gas emitting substance composite gas around the perimeter of the absorbent core 44 or in concentric rings can be used to determine a child's ability to hold a certain volume of fluid in his or her bladder before voiding, which can be useful during different stages of potty training. In some desirable aspects, the signal composite 88 will have approximately the same flexibility as the overall flexibility of the article 20. The form of the gas emitting substance in FIGS. 1 and 2 can be in the form of powders, particles, flakes, fibers, agglomerates, granules, spheres, tablets, capsules, coatings, or lotions and may or may not be encapsulated. In other embodiments, the gas emitting substance may be added to the absorbent article in the form of a coating, or a separate material such as a panty liner.

Because a large volume of gas is produced by the gas emitting substance contained in the composite, the wearer's or caregiver's ability to recognize when a liquid insult has occurred (and/or is occurring) will be enhanced due to how quickly the color change and/or signal alerts (visual, audio, vibratory) can be initiated. The gas emitting substance composite 88 can be positioned within the article 20 in any operative location such that a liquid insult can reach the gas emitting substance composite 88 which reaction will cause a large volume of gas generation. For example, in some aspects, the gas emitting substance composite 88 can be disposed adjacent to and in contact with the body-facing surface of an absorbent core 44. In other aspects, the gas emitting substance composite 88 can be disposed adjacent to and in contact with the garment-facing surface and/or the body-facing surface of a topsheet 42. In still other exemplary aspects, the gas emitting substance composite 88 can be disposed adjacent to and in contact with the body-facing surface or garment-facing surface of a surge layer, for example. Other configurations are also suitable for the invention as would be readily apparent to those skilled in the art so long as a liquid insult can come into contact with the gas emitting substance composite.

The gas emitting substance composite 88 of the present disclosure can be a laminate comprising a carrier substrate layer (not shown). The carrier substrate layer is provided by a separate web of material that can be at least partially or completely liquid permeable. The gas emitting substance may be placed inside the substrate layer. Suitable liquid permeable materials include tissue layers; nonwovens such as meltblown, coform, spunbond, spunbond-meltblown-spunbond (SMS), bonded-carded-web (BCW), woven fabric; perforated films; foam layers; and the like.

In some aspects, the gas emitting substance composite 88 can include particles or powders of the sodium bicarbonate/citric acid mix that which can be used to generate carbon dioxide upon the occurrence of a liquid insult in the absorbent article, although other non-toxic gas generating particles or powders may be used. In one embodiment, the gas emitting substance includes at least one acid and at least one base. The acid and base react together upon being wetted to produce a gas that may be, for example, carbon dioxide gas. The exact gas produced by the gas producing system is not critical, so long as the gas produced is substantially non-harmful to the skin of the wearer and there is a gas sensitive ink and non-contact gas sensor that can function with the gas generated. Note, however, that it is not necessary that a powder or particles of the mix be used, and the mix can be included in a lotion or other substance that is coated on the body-contacting surface of a non-woven. In general, the gas emitting substance composite 88 is responsive to contact with liquid insult such as urine, complex fluids or other aqueous body exudates to generate a gas such as carbon dioxide, for example.

Figure 3:
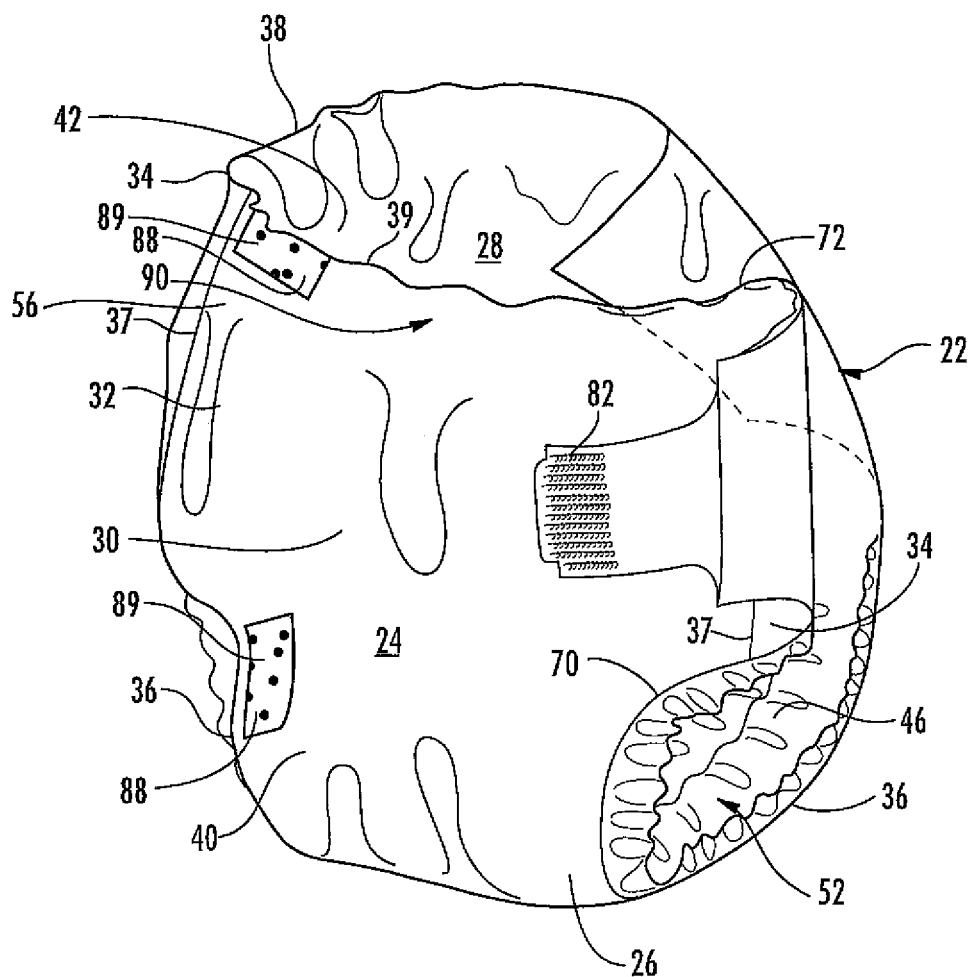
FIG. 3 is a perspective view of an absorbent article containing a gas emitting composition on the exterior surface of the absorbent article that emits a gas when the absorbent article to indicate fullness related to one or more liquid insults within the absorbent article.

FIG. 3 shows an absorbent article containing a gas emitting substance composite 88 on the exterior surface of the absorbent article that emits a gas when the liquid in the absorbent article reaches the exterior, such as at a side edge 36 or waist edge 38 to indicate fullness related to one or more liquid insults within the absorbent article. The exterior facing surface 89 is shown, although there is also a garment facing surface (not shown) that will first come into contact with an insult when the absorbent article is full and the insult has begun to leak outside the absorbent article. This will result in the gas emitting substance emitting a gas that can be detected by a device containing a gas sensitive composition. The gas sensitive composition may be unique from other gas sensitive compositions on the device or other devices nearby in order to distinguish between an insult and an absorbent article nearing its maximum absorbent capacity. The composite can be placed on the exterior of the absorbent article as shown, in addition to being placed at the direct insult region as in FIG. 1 or the perimeter of the absorbent core 44 as in FIG. 2. The ability to distinguish between insults and the absorbent article nearing its maximum absorbent capacity depends on the gas emitting substances used in each composite, the gas emitted from the gas emitting substance, and the gas sensitive ink used on the device such as a badge. As long as different signals, colors and/or images are given or displayed after an insult or due to fullness via the use of different inks or compositions, the ability to distinguish between events is possible.

Figure 4A:
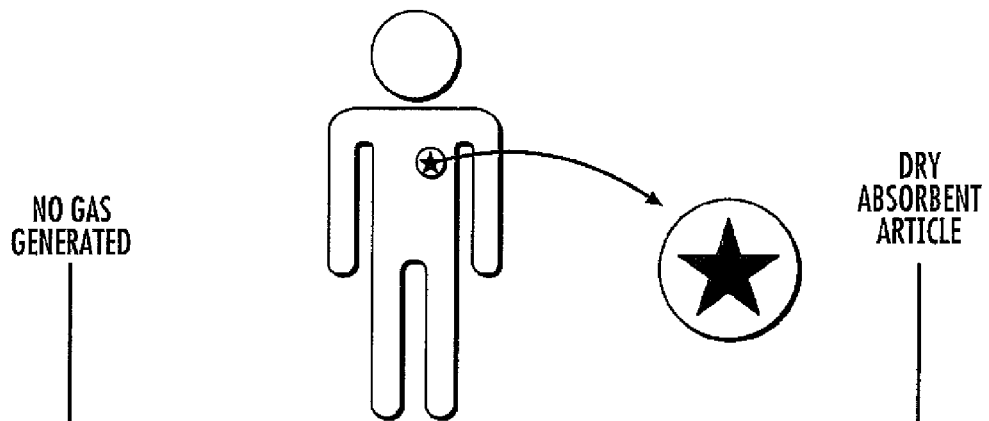
FIGS. 4A, 4B and 4C are comparison views of a device that a wearer or user of an absorbent article may wear or use to determine if a liquid insult has occurred and/or to determine fullness within the absorbent article.
Figure 4B:
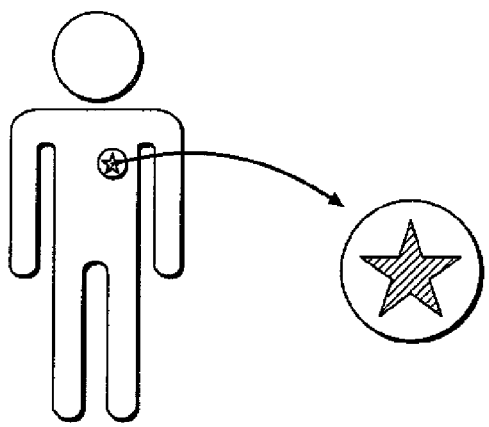
Figure 4C:
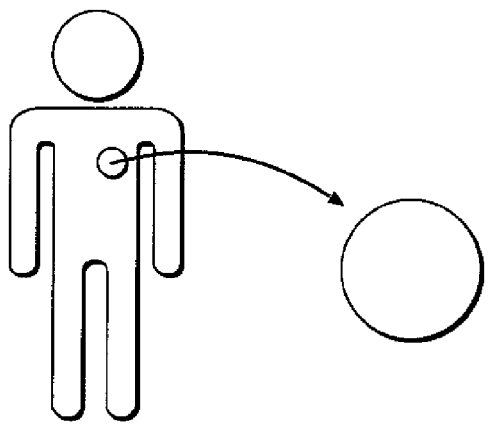

Referring to FIGS. 4A-4C, an illustration of an embodiment of a device incorporating a gas sensitive ink is shown attached to a child or other wearer of an absorbent article. Note, however, that the device need not be worn by the child or other wearer to be able to detect insults or fullness within the absorbent article as long as the device incorporating the gas sensitive ink can come into contact with a gas emitted by the gas emitting substance. Note also that more than one device can be used, and the device may incorporate more than one gas sensitive composition or ink in order to detect the occurrence of an insult or the fullness of the absorbent article. The device shown is a badge or button, but it can also be a watch, sticker, tattoo, or other device as long as it can incorporate one or more gas sensitive compositions/inks. The device incorporating a gas sensitive ink is shown in FIGS. 4A-4C, where at one extreme FIG. 4A shows a badge where there has not been a liquid insult or any generation of carbon dioxide gas and at the other extreme, FIG. 4C shows a badge where there has been a liquid insult resulting in a large generation of gas, which causes a color change in the device incorporating the gas sensitive composition. In FIG. 4A, the gas sensitive ink is deposited in the shape of a star and shows an initial strong/dark color while the absorbent article is dry and free of an insult. FIG. 4B shows changes in color intensity of the same gas sensitive composition immediately after being contacted by gas emitted from the absorbent article due to a liquid insult. FIG. 4C shows the rapid disappearance of the gas sensitive composition after being exposed to the gas emitted from the absorbent article after an insult. As is shown in FIG. 4, the color of the gas sensitive composition can disappear almost immediately after an absorbent article containing a gas emitting substance is contacted with a small volume of liquid. Even with a relatively small volume of liquid, the gas sensitive composition can communicate a visually observable signal due to the high volume of gas produced when a small volume of liquid contacts a gas emitting substance within the absorbent article. Although this embodiment shows an image quickly disappearing upon the occurrence of an insult, an image can appear upon the occurrence of an insult instead, or a combination or gradient of disappearing and appearing images can be used to indicate the presence of a liquid insult based on the type of gas sensitive compositions used and that are known to one of ordinary skill in the art. Additionally, various gas emitting substances and gas sensitive compositions can be used in combination with one or more devices to result in different color changes based on the presence of an insult within or the fullness/capacity of the absorbent article.

Figure 5:
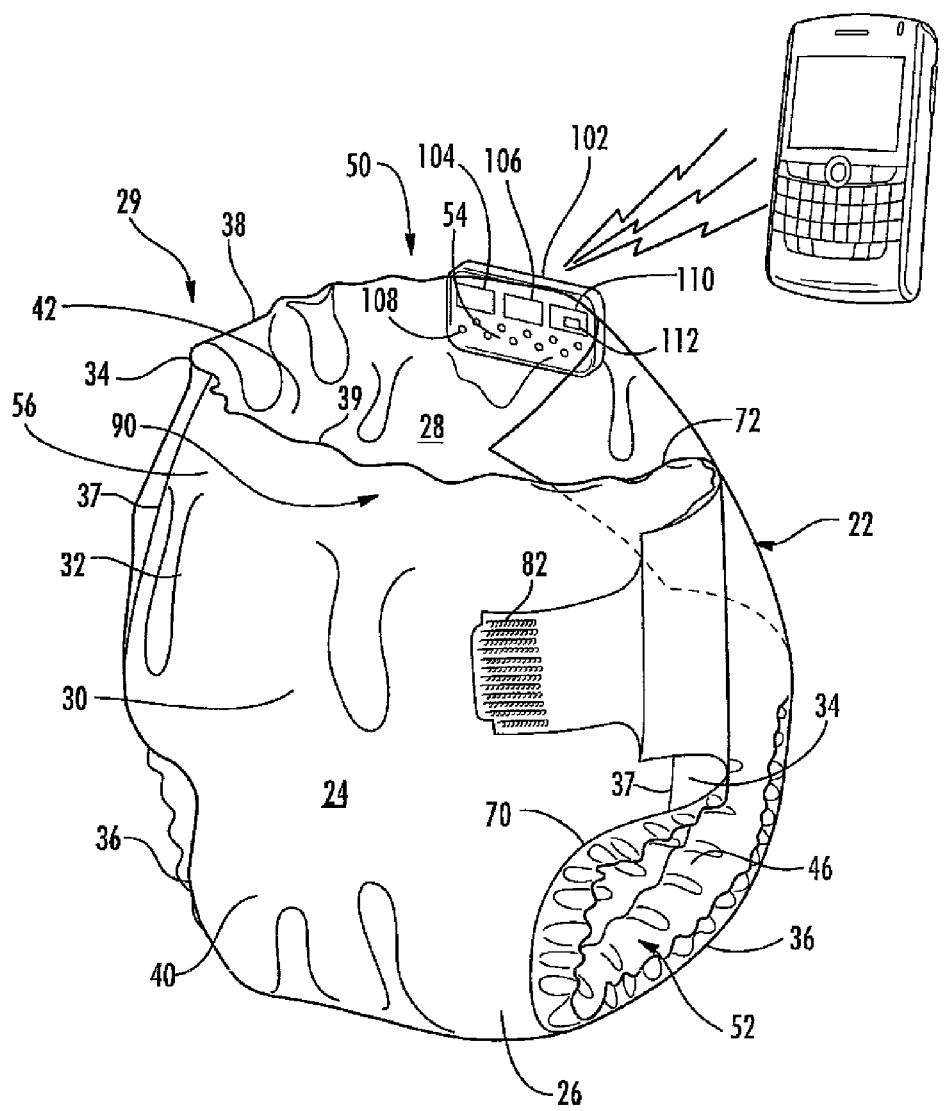
FIG. 5 is a perspective view of one embodiment of the present disclosure including one embodiment of a housing unit with a non-contact gas sensor, controller and signaling device that a wearer or user of an absorbent article may wear or use to determine if a liquid insult has occurred or to continuously monitor to determine how long the absorbent article has remained dry.

Referring to FIG. 5 for exemplary purposes, an absorbent article 20 that may be used during monitoring of insults within an absorbent article is shown. The absorbent article 20 includes many of the same components as shown in FIG. 1, which can be referred back to as the reference numerals are described, but FIG. 5 also shows the addition of a non-contact gas sensor, controller, and signaling device as discussed in more detail below. It is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present disclosure.

By way of illustration only, various materials and methods for constructing absorbent articles such as the absorbent article 20 of the various aspects of the present disclosure are described in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

An absorbent article 20 is representatively illustrated in FIG. 5 in a partially fastened condition. The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, which when worn, wholly or partially cover or encircle the waist or mid-lower torso of the wearer. The crotch region 26 generally is that portion of the absorbent article 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this embodiment, encompasses the front region 22, the back region 24, and the crotch region 26. Referring to FIG. 5, the chassis 32 includes an outer cover 40 and a bodyside liner 42 that may be joined to the outer cover 40 in a superimposed relation therewith by adhesives, ultrasonic bonds, thermal bonds or other conventional techniques. Referring to FIG. 5, the liner 42 may suitably be joined to the outer cover 40 along the perimeter of the chassis 32 to form a front waist seam and a back waist seam. The liner 42 may suitably be joined to the outer cover 40 to form a pair of side seams in the front region 22 and the back region 24. The liner 42 can be generally adapted, i.e., positioned relative to the other components of the absorbent article 20, to be disposed toward the wearer's skin during wear of the absorbent article. The chassis 32 may further include an absorbent structure disposed between the outer cover 40 and the bodyside liner 42 for absorbing liquid or solid body exudates exuded by the wearer, and may further include a pair of containment flaps 46 secured to the bodyside liner 42 for inhibiting the lateral flow of body exudates.

The elasticized containment flaps 46 as shown in FIG. 5 define a partially unattached edge which assumes an upright configuration in at least the crotch region 26 of the absorbent article 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 may also suitably include leg elastic members (not shown), as are known to those skilled in the art. The leg elastic members can be operatively joined to the outer cover 40 and/or the bodyside liner 42 and positioned in the crotch region 26 of the absorbent article 20. Note that although an absorbent article in the form of a training pant or diaper is shown, other absorbent articles such as bed mats or pads can also be used.

The leg elastic members can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the absorbent article 20 such as the absorbent structure 44 or the bodyside liner 42 by methods known in the art, such as by using an adhesive. A surge management layer helps to decelerate and diffuse surges or gushes of liquid or other waste that may be rapidly introduced into the absorbent structure of the article. Desirably, the surge management layer can rapidly accept and temporarily hold the liquid or other waste prior to releasing the liquid or other waste into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIG. 5, the absorbent article 20 may further include a pair of opposing elastic side panels 34 that are attached to the back region of the chassis 32. As shown particularly, the side panels 34 may be stretched around the waist and/or hips of a wearer in order to secure the garment in place. As shown in FIG. 5, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in FIG. 5, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIG. 5, the elastic side panels 34 may be connected by a fastening system to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the FIG. 5, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge (not shown), a leg end edge 70 disposed toward the longitudinal center of the diaper 20, and waist end edges 72 disposed toward a longitudinal end of the absorbent article. The leg end edges 70 of the absorbent article 20 may be suitably curved and/or angled to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present disclosure. Ultimately, the side panels 34 are generally aligned with a waist region 90 of the chassis 32.

The fastening system may include laterally opposite first fastening components 82 adapted for refastenable engagement to corresponding second fastening components (not shown). In the embodiment shown in the figures, the first fastening component 82 is located on the elastic side panels 34, while the second fastening component may be located on the front region 22 of the chassis 32. In one aspect, a front or outer surface of each of the fastening components includes a plurality of engaging elements. The engaging elements of the first fastening components 82 are adapted to repeatedly engage and disengage corresponding engaging elements of the second fastening components to releasably secure the article 20 in its three-dimensional configuration.

The fastening components may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

The first fastening components 82 may include hook fasteners and the second fastening components may include complementary loop fasteners. Alternatively, the first fastening components 82 may include loop fasteners and the second fastening components may be complementary hook fasteners. In another aspect, the fastening components can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

Figure 6:
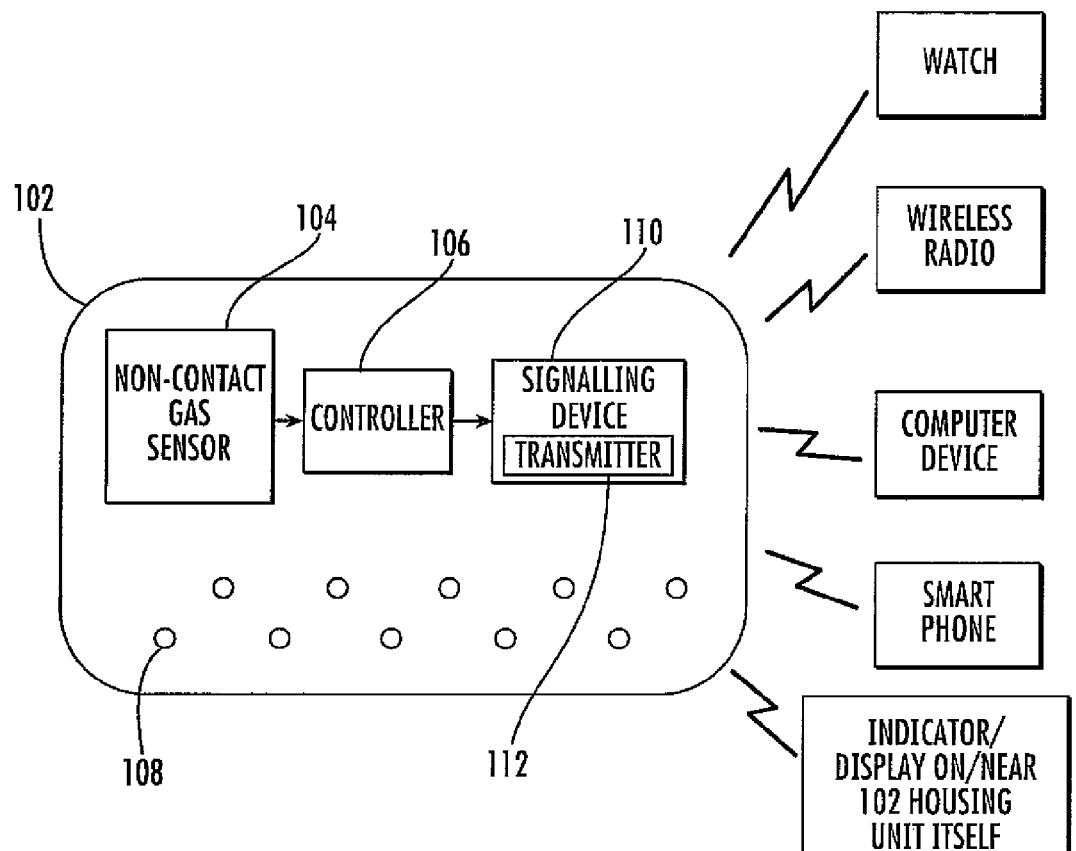
FIG. 6 is a block diagram of one embodiment of a housing unit which may contain a carbon dioxide sensor, a controller and a signaling device that may be located at or near the waist opening or edge of an absorbent article or may transmit a signal to a radio, a computer device, a smart phone or indicator/display that is on or near the housing unit.

Referring to FIGS. 5 and 6, for exemplary purposes, the non-contact gas sensor 104, controller 106 and signaling device 110 that are part of the absorbent article system may be contained in a housing unit 102, which is shown attached to the absorbent article 20. In this embodiment, the signaling device generally 110 includes a transmitter 112 that communicates with a receiver 114. The receiver can be a watch, radio, a computer device or a smart phone. The transmitter 112 can be housed in the housing unit 102 with the non-contact gas sensor 104 and controller 106. When an insult is present in the absorbent article 20, the controller 106 detects changes in gas levels monitored by the non-contact gas sensor 104, which, in turn, activates the signaling device 110. In one embodiment, the non-contact gas sensor is able to monitor gas levels through visible openings 108 in the housing unit 102. In another embodiment, it is possible that the housing unit could be constructed of a porous material so that a sufficient amount of gas could enter into the housing unit, to allow the non-contact gas sensor to detect the presence of any gases associated with the gas emitting substance.

In still another embodiment, the transmitter 112 may send a wireless signal or alert to the receiver 114 which then indicates to a user that a liquid insult is present in the absorbent article. The signaling device 110 can emit an audible signal, a visual signal and/or a vibratory signal in order to indicate to the user that an insult has been detected. Different alerts or combinations of alerts can also be used to indicate that the absorbent article has remained continuously dry for a certain amount of time. The audible signal, for instance, may be as simple as one or more beeps to perhaps emitting a musical tune. Similarly, if the signaling device 110 issues a visible signal, the visible signal may comprise a few lights or an interactive display. In still another embodiment, the receiver 114 of the signaling device 110 may be configured to vibrate when an insult has been detected.

As described above, the signaling device 110 can be configured to indicate the presence of any insult within the absorbent article 20. The insult may comprise, for instance, urine and/or runny bowel movement. In the embodiment shown in FIGS. 5 and 6, the signaling device 110 includes a transmitter 112 in combination with a receiver 114. It should also be understood, however, that the signaling device may be a single unit that is located on or near to the absorbent article 20. For example, the signaling device may be attached to the absorbent article and issue a visible signal and/or an audible signal from the article itself so that the wearer and/or another person such as a caregiver who is close by can be notified of an insult. Additionally, it should be understood that data from the signaling device may be transmitted to a watch, radio, computer or smartphone through a wireless network or other means. Further, it should be understood that the signaling device can be deactivated or removed to take a break from potty training or when it would be inappropriate for the signaling device to notify the child/user or parent/caregiver of an insult. Moreover, the signaling device 110 can be used in conjunction with the gas sensitive ink described above, which can also be easily removed if a break is desired or its use is not appropriate.

In the embodiment shown in FIG. 6, the housing unit 102 that may be attached to an absorbent article contains a non-contact gas sensor 104 which could have at least one individual sensor 100, a controller 106 and a signaling device 110, which can include a transmitter 112 and a receiver 114. Additionally, openings 108 may be present on the signaling device that allow the non-contact gas sensor 104 to be exposed to a sufficient gas sample in order to detect the presence of a gas generated by a liquid insult's reaction with a gas emitting substance within the absorbent article 20. In another embodiment, a gas sample can reach the non-contact gas sensor 104 by traveling through a housing unit made of a porous material. In yet another embodiment of a housing unit, if the signal is being expressed to the wearer, the receiver is present on or near the housing unit itself. Meanwhile, if the signal is being expressed to another user, such as a caregiver, through means such as a wireless radio, a computer device or a smart phone, the receiver may send a wireless signal to a transmitter located some distance away from the receiver and signaling device. When gas concentration threshold levels are monitored and detected, then the controller 106 may read and compute the levels in order to make a decision to signal an alert to a user and/or caregiver by means of an auditory, visual, and/or vibratory signal, which may or may not be transmitted to a wireless radio, smart phone, computer device, or others means of display.

Figure 7:
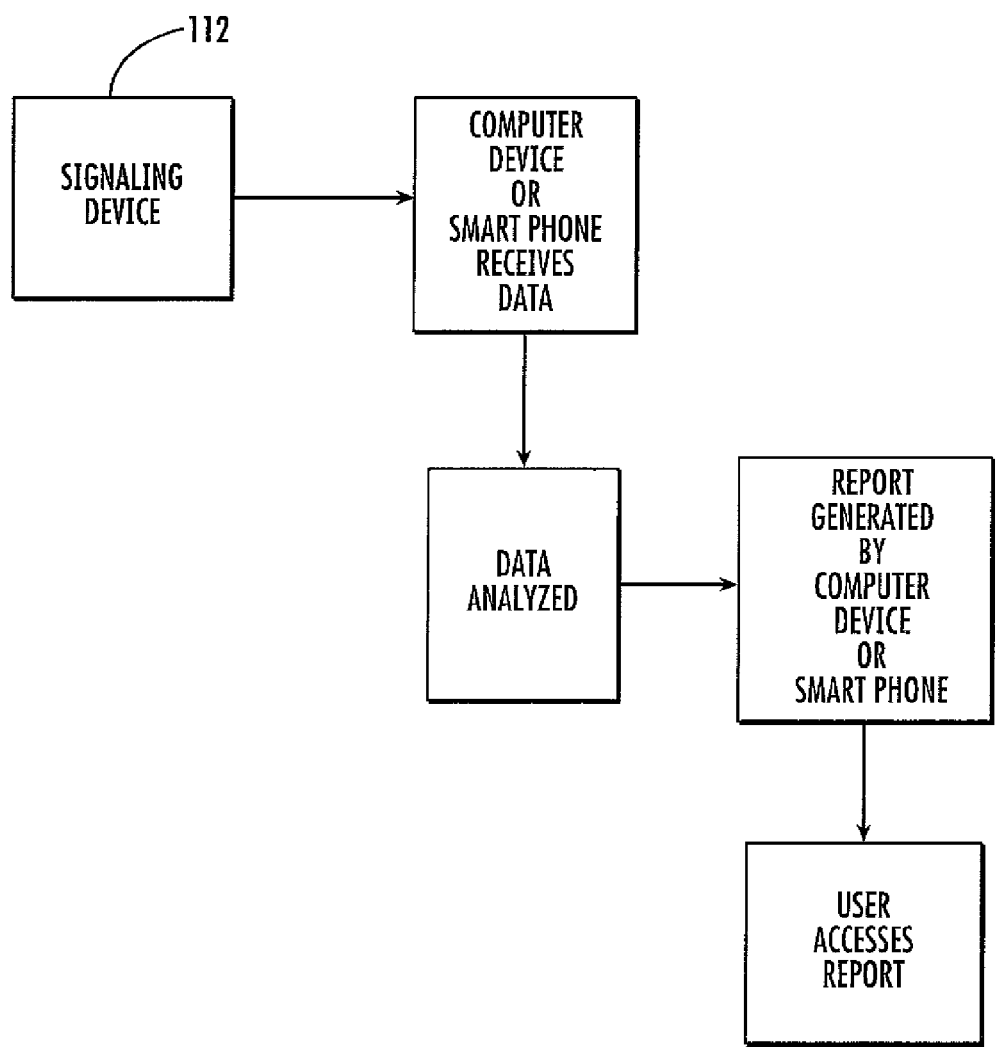
FIG. 7 is a block diagram showing how an embodiment of a signaling device can transmit data to a computer device or smart phone, which can then signal the user and/or caregiver of an insult and generate data reports for a user or caregiver to access.

FIG. 7 is a block diagram describing how a signaling device may connect with a computer device or smart phone, which can then generate data reports for the user/parent/caregiver to access. In one embodiment, after a non-contact gas sensor has monitored at least one gas level and a controller has detected an increase above a threshold level through pattern recognition and data analysis to indicate the presence of a liquid insult, a signaling device may transmit an alert to a location at or near the waist opening of an absorbent article to inform the wearer and/or a caregiver who is close by. In another embodiment, the user or caregiver may wish to receive an alert at a remote location, such as via a wireless radio. In still another embodiment, the user and/or caregiver may wish to have the alerts sent to a computer device or smart phone. When sent to a computer device or smart phone, the alert may be visual and/or auditory, or the alert may be stored as data along with previous and future alerts. In this manner, the user and/or caregiver may be able to call up the data from the computer device or smart phone to determine the number of insults within an absorbent article that is being monitored. The user and/or caregiver can view a report generated on a computer device or smartphone that was transmitted to the computer device or smartphone from the signaling device and can access the report for various uses.

In one embodiment, the caregiver receives a report to determine how well the wearer's toilet training is progressing by looking at data over several hours, days, weeks, months, or other appropriate time frame, such as time of day (night, nap time, etc.). The user and/or caregiver can be provided with data to see if there are any changes in the length that an absorbent article is continuously dry to determine if the user/wearer is learning how to potty train or ready to begin potty training as it requires the ability to hold volume in the bladder for a longer time. From this information provided by the described method, the caregiver can adjust his or her approach to toilet training.

Different attachment mechanisms for attaching the housing unit containing the non-contact gas sensor, controller and signaling device about the waist opening of an absorbent article will now be described in detail with respect to FIGS. 8 and 9. It should be noted that while the attachment mechanisms shown in the figures below generally incorporate two plates or sides, the non-contact gas sensor 104 should be positioned so that it is on a plate or side facing the interior of the absorbent article in order to be able to detect gases and changes in humidity and temperature due to a urine and/or bowel movement insult.

Figure 8:
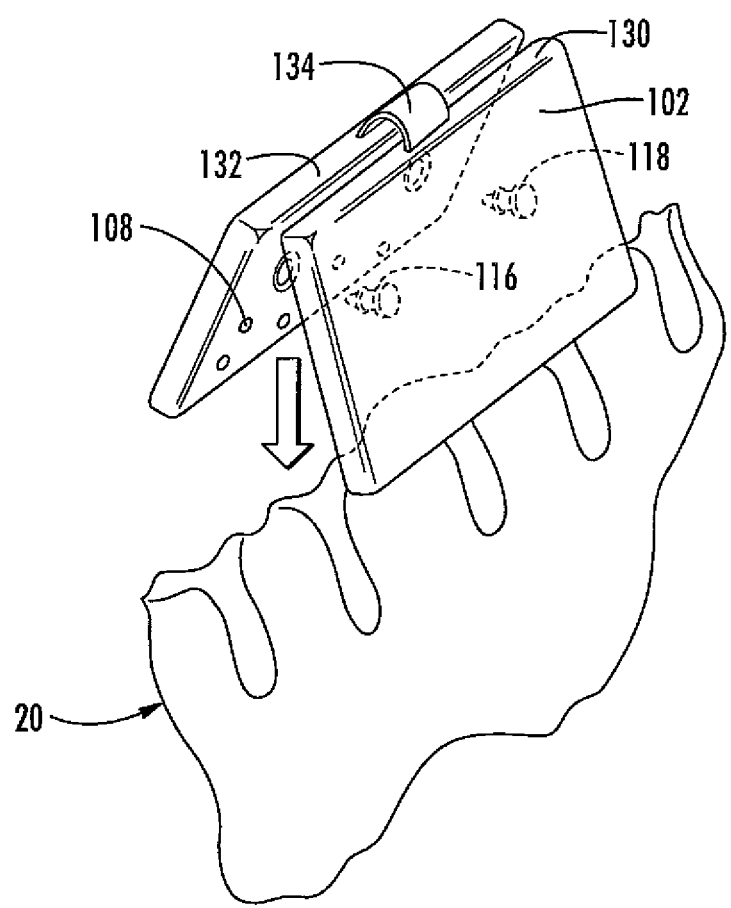
FIG. 8 is an embodiment of an attachment mechanism for attaching a housing unit to an absorbent article in accordance with the present disclosure.

Referring to FIG. 8, an embodiment of an attachment mechanism that may be used to attach the housing unit 102 around the waist opening of an absorbent article 20 is shown. Note also that the absorbent article may not have a waist opening if it is a bed pad, for example, so the housing unit may be attached to another edge of an absorbent article besides a waist opening. In this embodiment, the housing unit 102 comprises a first exterior plate 130 spaced from a second interior plate 132. The first exterior plate 130 should be placed on the outside of the absorbent article 20. In one embodiment, the second interior plate 132 can be placed on the inside of the absorbent article 20 so that the gases emitted from the absorbent article 20 after an insult will be able to reach the openings 108. Once the gases reach the openings 108 in the housing unit 102, then the non-contact gas sensor 104 can monitor gas concentration levels, and then the controller 106 can detect any changes in the gas concentration levels due to an insult. Additionally, an end of the first exterior plate 130 may be pivotally connected to an end of the second interior plate 132 about a hinge 134. In this manner, the housing unit 102 may be positioned securely about a waist opening or other edge of an absorbent article such as a bed pad or it may alternatively be incorporated into the absorbent article. The housing unit 102 may also be positioned securely on the clothing or the child/wearer or elsewhere, so long as the non-contact gas sensor 104 is in close proximity to the absorbent article to detect any gases emitted from the gas emitting substance.

In order to attach the housing unit 102 to the absorbent article 20, the first exterior plate 130 includes a pair of prongs that serve as the first terminal 116 and the second terminal 118. As shown in the drawing, the plates 130 and 132 of the housing unit 102 are configured to be placed over an edge of the chassis, such as about a waist opening, and brought together such that the prongs 116 and 118 pierce the chassis and lock into place.

Figure 9:
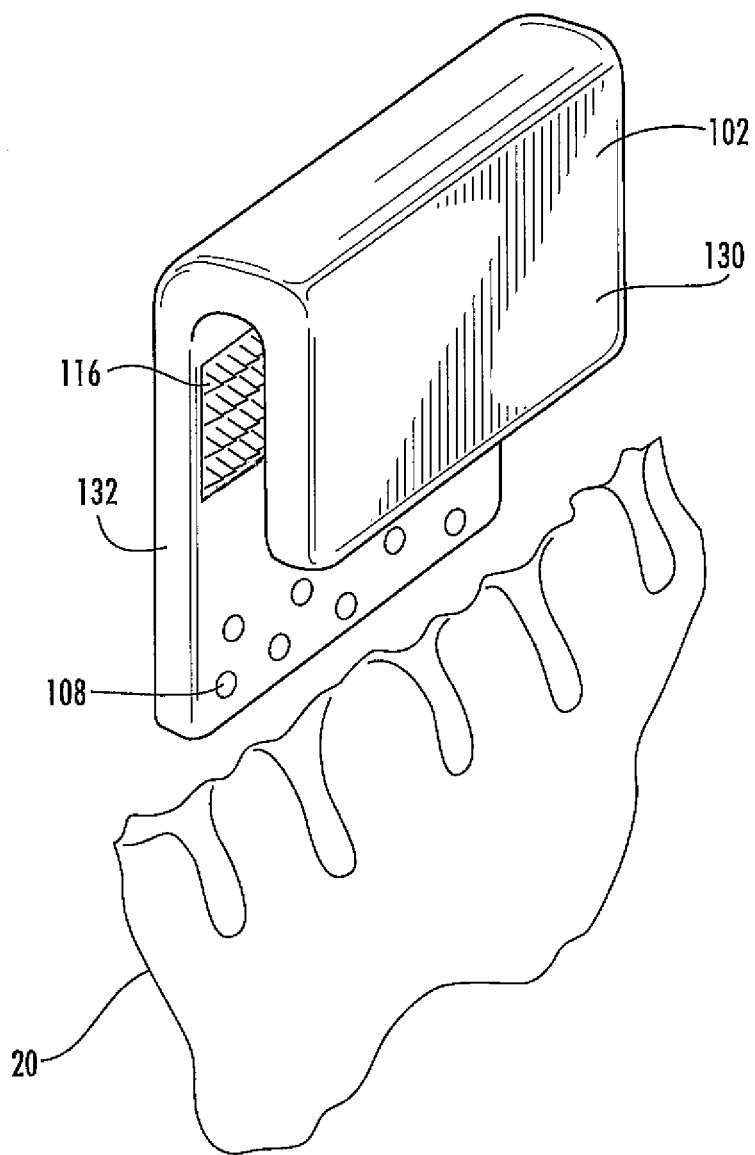
FIG. 9 is another embodiment of an attachment mechanism for attaching a signaling device to an absorbent article in accordance with the present disclosure.

Referring to FIG. 9, still another embodiment of a housing unit 102 connected to an absorbent article 20 is shown. In this embodiment, the housing unit 102 may include a clip device comprising a first exterior plate 130 spaced from a second interior plate 132. The plates 130 and 132 are integral with each other and are made from a flexible material that allows the plates to be separated from each other for placing the signaling device over an edge of an absorbent article. Once the plates, however, are placed on the absorbent article, the plates are biased towards each other for holding the signaling device in place. In this manner, the housing unit 102 has a paper clip-like structure. In this manner, the housing unit 102 may be positioned securely about a waist opening or other edge of an absorbent article such as a bed pad or it may alternatively be incorporated into the absorbent article. The housing unit 102 may also be positioned securely on the clothing or the child/wearer or elsewhere, so long as the non-contact gas sensor 104 is in close proximity to the absorbent article to detect any gases emitted from the gas emitting substance.

In one embodiment, placing the second interior plate 132 on the inside of the absorbent article 20 allows the gases emitted from the absorbent article 20 after an insult to reach the openings 108 in the housing unit 102. Once the gases reach the openings 108, then the non-contact gas sensor 104 can monitor gas concentration levels, and then the controller 106 can detect any changes in the gas concentration levels due to an insult.

In the embodiments illustrated in FIGS. 8 and 9, the housing unit 102 can be made from any suitable material. For example, in one embodiment, the housing unit can be made from a flexible plastic material. It should be understood, however, that elastomeric materials and metal materials may also be used. Additionally, at least a portion of the housing unit may be made of porous or mesh-like material to allow for the non-contact gas sensor to receive a sufficient gas sample to monitor gas levels above a threshold level.

As described above, the present disclosure is particularly directed to a method for interactive potty training where a bodily waste/exudate indicating system may be able to detect the presence of liquid insult in an absorbent article 20 and discriminate between urine and bowel movement. The remaining materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbonded polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure (not shown). A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure may be disposed between the outer cover 40 and the bodyside liner 42. The absorbent structure can be any structure or combination of components which are generally compressible, conformable, non-irritating to a wearer's skin, and capable of absorbing and retaining liquids and certain body wastes. For example, the absorbent structure may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 100 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, various superabsorbent materials are available from Evonik Industries, Germany.

After being formed or cut into a desired shape, the absorbent web material may be wrapped or encompassed by a suitable tissue or meltblown web or the like wrap sheet that aids in maintaining the integrity and shape of the absorbent structure.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed is:

1. A system for detection and monitoring of body exudates, comprising:
   an absorbent article;
   a first gas emitting substance within the absorbent article, wherein the first gas emitting substance emits a first gas when the absorbent article is contacted with a liquid insult;
   a color-changing device in association with the absorbent article, comprising a first gas sensitive composition, wherein the appearance of the color-changing device changes when the device is contacted with the first gas, wherein the color-changing device is a badge, watch, or sticker worn outside a wearer's clothing; and a second gas emitting substance, wherein the second gas emitting substance emits a second gas when the absorbent article is nearing its maximum absorbent capacity, wherein the appearance of the color-changing device changes in a first manner when the device is contacted with the first gas, and wherein the appearance of the color-changing device changes in a second manner when the device is contacted with the second gas.

2. A system as defined in claim 1, wherein the first gas emitting substance comprises aldehydes, benzyl ester, phenol, iso rose, sodium bicarbonate, calcium bicarbonate, or potassium bicarbonate.

3. A system as defined in claim 1, wherein the first gas emitted from the first gas emitting substance is carbon dioxide.

4. A system as defined in claim 3, wherein the first gas emitting substance comprises sodium bicarbonate and citric acid.

5. A system as defined in claim 1, wherein the first gas emitting substance is in a form including powders, particles, flakes, fibers, agglomerates, granules, spheres, tablets, capsules, coatings, or lotions.

6. A system as defined in claim 1, wherein the first gas sensitive composition comprises a pH indicator, a humectant, a basic compound, a short-chain alcohol, and water.

7. A system as defined in claim 6, wherein the pH indicator includes phenolphthalein, thymolphthalein, α-naphtholphthalein, or o-cresolphthalein; the humectant includes ethanolamines, (poly)alkyleneglycols, or glycerol; the basic compound includes sodium hydroxide, sodium carbonate, or sodium acetate; and the short-chain alcohol includes methanol, ethanol, propanol, or butanol.

8. A system as defined in claim 1, further comprising a non-contact gas sensor, wherein the non-contact gas sensor monitors a gas concentration level of the first gas.

9. A system as defined in claim 8, further comprising:

a controller, wherein the controller is configured to detect a change above a threshold level in the gas concentration level of the first gas when the absorbent article is contacted with the liquid insult, wherein an increase in the gas concentration level of the first gas indicates that a liquid insult has occurred, and wherein the controller is configured to continuously monitor a dry time within the absorbent article; and a signaling device, wherein the signaling device alerts a wearer, user, or combination of both of the presence of a liquid insult within the absorbent article, the amount of time the absorbent article has been continuously dry, or both.

10. A system as defined in claim 9, wherein the signaling device generates at least one alert selected from an auditory signal, a vibratory signal, a visual signal, or a combination thereof, and wherein the at least one alert is transmitted to a watch, radio, smart phone, or computer device at a remote location.

11. A system as defined in claim 10, wherein the computer device, smart phone, or a combination of both is adapted to receive data from the signaling device, generate at least one report utilizing at least a portion of the data, and provide the user access to the data and the at least one report.

12. A system as defined in claim 10, wherein the signaling device can be deactivated at or near the absorbent article or remotely.

13. A system as defined in claim 9, wherein a housing unit containing the non-contact gas sensor, controller, and signaling device is in close enough proximity to the absorbent article to detect the at least one gas.

14. A method of transmitting information to a user of an absorbent article, a caregiver, or a combination of both, comprising:

monitoring for a presence of a first gas emitted from a first gas emitting substance within the absorbent article, wherein the first gas emitting substance emits the first gas when the absorbent article is contacted with a liquid insult, wherein the monitoring occurs via a color-changing device, wherein the color-changing device comprises a first gas sensitive composition, further wherein the color-changing device is a badge, watch, or sticker worn outside a wearer's clothing;

alerting the user, caregiver, or a combination of both of the liquid insult via a color change;

monitoring for a presence of a second gas, wherein a second gas emitting substance emits the second gas when the absorbent article is nearing its maximum absorbent capacity; and providing information to the user, caregiver, or both, wherein the information is provided by the color-changing device, wherein the color-changing device comprises a second gas sensitive composition, wherein the appearance of the color-changing device changes in a first manner when the device is contacted with the first gas, and wherein the appearance of the color-changing device changes in a second manner when the device is contacted with the second gas.

15. A method as defined in claim 14, wherein a non-contact gas sensor detects the presence of the first gas when the absorbent article is contacted with the liquid insult; wherein a controller is configured to detect a change above a threshold level in a gas concentration level of the first gas; wherein the controller is configured to continuously monitor the dry time within the absorbent article; and wherein a signaling device alerts the wearer, user, or both of the presence of the liquid insult within the absorbent article, the amount of time the absorbent article has been continuously dry, or both.

16. A method as defined in claim 15, wherein the signaling device generates at least one alert selected from an auditory signal, a vibratory signal, a visual signal, or a combination thereof, and wherein the alert is transmitted to a watch, radio, smart phone, computer device, or a combination thereof at a remote location.

17. A method as defined in claim 16, wherein the at least one alert is perceptible outside the absorbent article and wherein the at least one alert is perceptible outside an article of clothing worn by the wearer.

18. A method as defined in claim 16, wherein the at least one alert is deactivated at or near the absorbent article or remotely.

19. A method as defined in claim 16, wherein the computer device or smart phone is adapted to receive data from the signaling device, generate at least one report utilizing at least a portion of the data, and provide the user access to the data and the at least one report.

20. A method as defined in claim 19, wherein the user, caregiver, or a combination of both is provided with information from the at least one report to indicate the number of insults contained within an absorbent article.

21. A system as defined in claim 1, wherein the device is worn at a distance of up to about 12 inches away from the absorbent article.

22. A method as defined in claim 19, wherein the device is worn at a distance of up to about 12 inches away from the absorbent article.

\* \* \* \* \*

UNITED STATES PATENT AND TRADEMARK OFFICE
CERTIFICATE OF CORRECTION

| | | |
|---|---|---|
| PATENT NO. | : 8,816,149 B2 | Page 1 of 1 |
| APPLICATION NO. | : 13/283669 | |
| DATED | : August 26, 2014 | |
| INVENTOR(S) | : Kathy Geralyn Richardson et al. | |

It is certified that error appears in the above-identified patent and that said Letters Patent is hereby corrected as shown below:

On the title page, item (56), the following reference to be included under References Cited - U.S. Patent Documents 2012/0227983 A1   9/2012   Lymberopoulos et al.

Signed and Sealed this
Twenty-third Day of December, 2014

Michelle K. Lee
*Deputy Director of the United States Patent and Trademark Office*